(12) United States Patent
Honarbakhsh et al.

(10) Patent No.: US 11,457,854 B2
(45) Date of Patent: Oct. 4, 2022

(54) COMPUTER IMPLEMENTED METHOD AND SYSTEM FOR AIDING MAPPING HEART RHYTHM ABNORMALITIES

(71) Applicant: RHYTHM AI LTD, Witney (GB)

(72) Inventors: Shohreh Honarbakhsh, Witney (GB); Ross Hunter, Witney (GB); Richard Schilling, Witney (GB); Malcolm Finlay, Witney (GB)

(73) Assignee: RHYTHM AI LTD, Witney (GB)

( * ) Notice: Subject to any disclaimer, the term of this patent is extended or adjusted under 35 U.S.C. 154(b) by 0 days.

(21) Appl. No.: 17/466,919

(22) Filed: Sep. 3, 2021

(65) Prior Publication Data
US 2022/0054070 A1 Feb. 24, 2022

Related U.S. Application Data

(63) Continuation of application No. PCT/GB2020/052734, filed on Oct. 29, 2020.

(30) Foreign Application Priority Data
Oct. 29, 2019 (GB) ..................... 1915680

(51) Int. Cl.
*A61B 5/00* (2006.01)
*A61B 5/364* (2021.01)
(Continued)

(52) U.S. Cl.
CPC .............. *A61B 5/364* (2021.01); *A61B 5/053* (2013.01); *A61B 5/283* (2021.01); *A61B 5/742* (2013.01); *G16H 50/20* (2018.01)

(58) Field of Classification Search
CPC . A61B 5/364; A61B 5/347–366; A61B 5/367; A61B 5/053; A61B 5/283; A61B 5/742; G16H 50/20
See application file for complete search history.

(56) References Cited

U.S. PATENT DOCUMENTS

2020/0359924 A1* 11/2020 Finlay ................... A61B 5/287

FOREIGN PATENT DOCUMENTS

| EP | 3192438 A1 | 7/2017 |
| EP | 3192443 A1 | 7/2017 |

(Continued)

OTHER PUBLICATIONS

Shohreh Honarbakhsh et al, "Development, in vitro validation and human application of a novel method to identify arrhythmia mechanisms: The stochastic trajectory analysis of ranked signals mapping method", Journal of Cardiovascular Electrophysiology.,vol. 30, No. 5, Mar. 5, 2019 (Mar. 5, 2019), p. 691-701.

*Primary Examiner* — Scott M. Getzow
(74) *Attorney, Agent, or Firm* — Leason Ellis LLP

(57) ABSTRACT

A computer implemented method and system are described that identify one or more regions of the heart responsible for supporting or initiating abnormal heart rhythms. Electrogram data is used that has been recorded from a plurality of electrodes on multipolar cardiac catheters obtained from a corresponding series of sensing locations on the heart over a recording time period. The method includes the steps of: identifying, from the electrograms, regions within a chamber of the heart which have electrical activation sequences which characterize them as potential drivers of abnormal heart rhythms,
for each sensing location at or substantially about said region, determining from predominant activations, an earliest activating electrode site;
for each determined earliest activating electrode site:
calculating a value for each of a plurality of modifiers associated with the electrode site, the modifiers being determined from the electrogram data for the site, tissue characteristics of the site or anatomical characteristics of the site;
determining a ranking factor calculated from the plurality of modifiers;

(Continued)

ranking the each of said earliest activating electrode sites in dependence on its ranking factor; and, outputting data identifying said regions, the data varying prominence of each of the determined earliest activating electrode sites in dependence on said ranking.

25 Claims, 33 Drawing Sheets

(51) Int. Cl.
*G16H 50/20* (2018.01)
*A61B 5/283* (2021.01)
*A61B 5/053* (2021.01)

(56) References Cited

FOREIGN PATENT DOCUMENTS

| | | |
|---|---|---|
| WO | WO 2003/089997 A2 | 10/2003 |
| WO | WO 2013/192459 A1 | 12/2013 |
| WO | WO 2015/153797 A1 | 10/2015 |

* cited by examiner

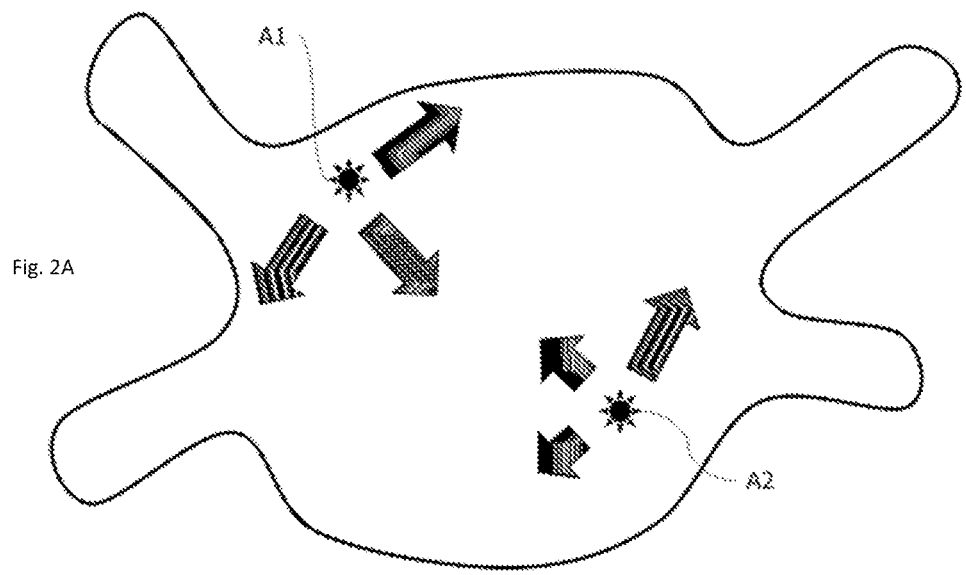

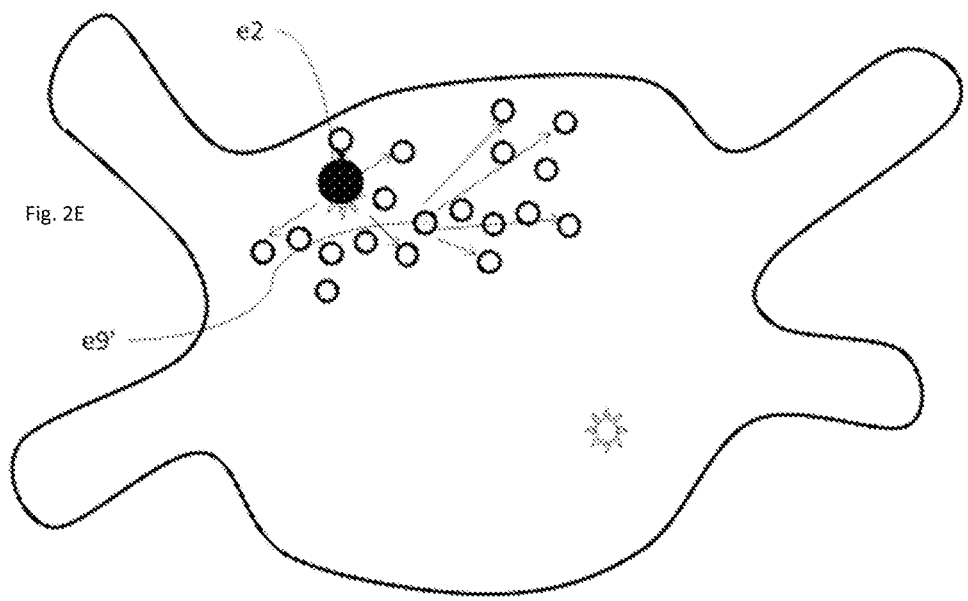

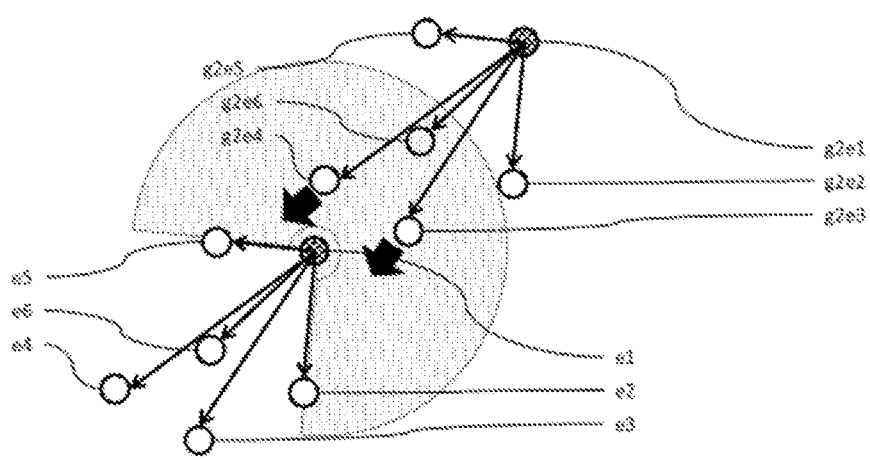

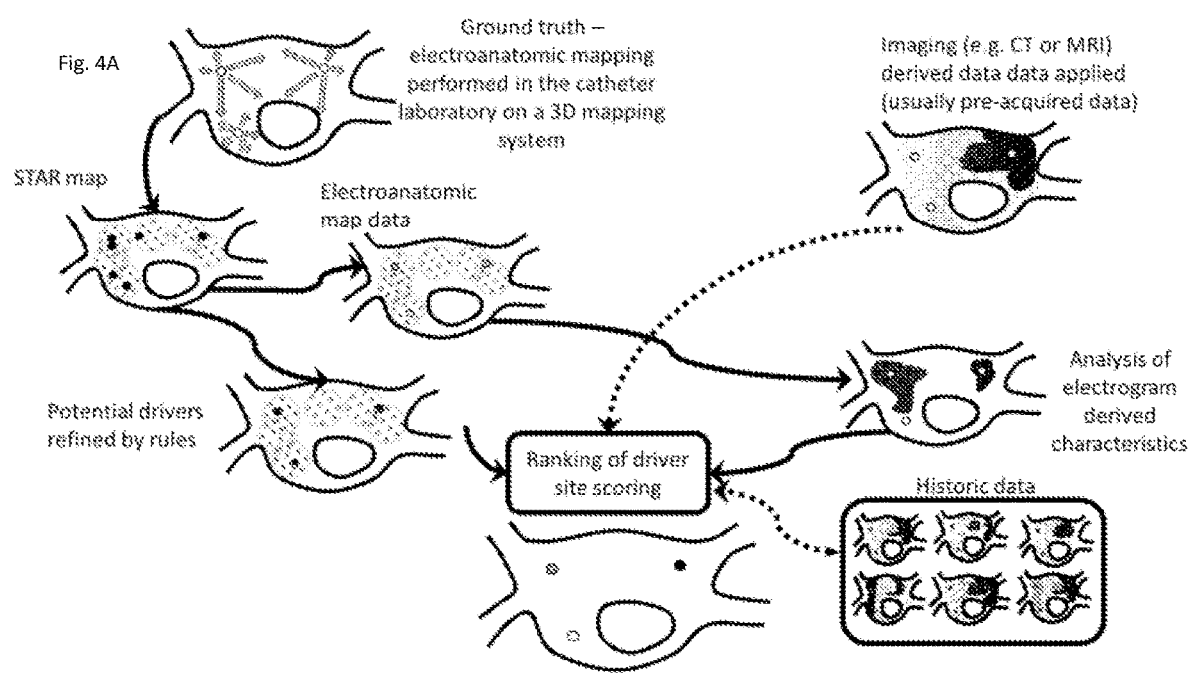

COMPUTER IMPLEMENTED METHOD AND SYSTEM FOR AIDING MAPPING HEART RHYTHM ABNORMALITIES

CROSS-REFERENCE TO RELATED APPLICATIONS

This application is a continuation of International Patent Application No. PCT/GB2020/052734, filed Oct. 29, 2020 which claims priority to Great Britain Application No. 1915680.1, filed Oct. 29, 2019, the contents of all of which are hereby incorporated by reference in their respective entireties.

FIELD OF THE INVENTION

The present invention relates to a computer implemented method and system for aiding mapping heart rhythm abnormalities and in particular to methods and systems to identify areas of the heart that are statistically likely to be driving abnormal heart rhythms.

BACKGROUND TO THE INVENTION

The present application is related to the earlier co-pending applications Publication Nos. WO 2019/206908 and GB 2573109, the contents of which are hereby incorporated by reference. These applications describe systems and methods for Stochastic Trajectory Analysis of Ranked Signals (STAR) mapping which is referenced below. While embodiments may use STAR mapping, as discussed below either approaches are also possible.

Atrial fibrillation (AF) is the most common sustained heart rhythm abnormality. Its incidence is increasing partly due to the aging population and it has been referred to as a growing epidemic. AF results in irregular contractions of the heart causing unpleasant symptoms of palpitations and increasing the risk of stroke, heart failure (HF) and death. Percutaneous catheter ablation (CA) is a safe treatment option in symptomatic patients with AF. The success rate of these procedures has improved with time due to the better understanding of AF, development of new techniques and technology, and greater physician experience. However, the success rate of these procedures still only remains between 50 and 70%. A major reason for the difficulties found in targeting the specific sites responsible for the persistence and maintenance of AF (hereafter referred to as AF drivers) is the irregular and chaotic nature of activation wavefronts in atrial fibrillation. The constant meandering and instability of individual rotational, re-entry or focal activations makes interpretations of activation sequences very complex.

More recently, a number of computational and electro-anatomical methods have been developed allowing electrical data (i.e. electrograms) recorded from within the atria to be presented to the physician in such a way that particular "driver" areas might be recognized. These drivers might also be easier or harder to recognize depending on the relationship between the frequency of the driver and the frequency of activations from non-driver random and chaotic activity. Panoramic mapping techniques attempt to address this issue. Here, multipolar catheters are inserted into the cardiac chamber of interest and the signals from across the chamber are acquired simultaneously. Examples of this include non-contact mapping (Ensite, Abbott Medical; alternatively Acutus Medical), and particular 2D and 3D contact mapping methods (e.g. Cartofinder, Biosense Webster, J&J; Topera, Abbott Medical; Rhythmia, Boston Scientific).

Evidence is conflicting as to whether electrogram characteristics are useful as surrogate markers for localized drivers in persistent AF in humans. These may be termed atrial fibrillation drivers (AFD)s. It is understood that a single AFD may give rise to a regular, non-fibrillatory arrhythmia, therefore AFD may be taken to indicate an Atrial Fibrillation/Arrhythmia Driver. Whilst features of organization of electrograms have better identified sites that play a mechanistic role in AF, markers of rapidity have been less reliable. Optical mapping studies in animals have shown that AF is maintained by sites demonstrating fastest cycle lengths (CL) and highest dominant frequency (DF), however, in humans this has proven to be a poor predictor of sites that support AF. The poor correlation may be because of the lack of spatiotemporal stability of drivers in AF, which may explain the apparent inconsistency of sites of rapidity. In addition, optical mapping studies in animals have shown intra-atrial high to low frequency gradients at rotor sites. Whilst frequency gradients have also been demonstrated in humans with AF these have been confined to inter-atrial gradients.

The STAR Mapping Method

The STAR mapping method has been described in detail in the above-mentioned patent applications, and was validated by mapping in vitro and in vivo by mapping atrial tachycardias (AT) before being used to map AF. In brief, the principle of the STAR mapping method is to use comparison of timings of multiple electrograms to establish the individual wavefront trajectories associated with AF. This is then used to identify regions of the atrium that most often precede activation of neighboring areas. By gathering data from many activations, a statistical model can be formed. This permits regions of the atrium to be ranked according to the amount of time that activations precede those of adjacent regions. Unipolar activation timing is typically taken as the maximum negative deflection (peak negative dv/dt), however activation timings may be derived from other methods such as dipole density or peak bipolar or resolved omnipolar voltage. Through utilizing pre-defined refractory periods the mapping method avoids assigning activations from separate wavefronts or fractionated electrograms. Electrode timing relationships that are implausible due to conduction velocity restraints are also excluded by the mapping method.

One form of a STAR map display consists of color-coded electrode positions projected on to a replica of the patient's atrial geometry created in a standard 3D mapping system. Each color represents the proportion of time the electrode spends leading in relation to the other paired electrodes as highlighted by the color scale on the right-hand side of the STAR maps.

Problem with Current Methodology

Mapping systems that seek to identify the proportion of times an electrode is "leading" in relation to its adjacent electrodes can be used to produce a global distribution of ranked sites which are potential AF drivers (AFDs) when using a basket to map the atria. However, for sequential high density mapping techniques, no information is provided as to the relative importance of early sites between one another. For instance, a number of sites might all be seen to be leading.

A further problem with analysis of sequentially acquired data relates to the complexity of interpretation of sites designated as leading on the edge of an acquisition area. This is exemplified in FIG. 1. A rule-based method of interpretation of such data is advantageous as it allows for automated interpretation to take place, and removal or reducing the prominence of display of passively activated sites on the edge of an acquisition reduces the areas which would be highlighted as potential driver sites.

Statement of Invention

According to an aspect of the present invention, there is provided a computer implemented method to identify one or more regions of the heart responsible for supporting or initiating abnormal heart rhythms, the computer implemented method using electrogram data recorded from a plurality of electrodes on multipolar cardiac catheters obtained from a corresponding series of sensing locations on the heart over a recording time period, the method including the steps of:

identifying, from the electrograms, regions within a chamber of the heart which have electrical activation sequences which characterize them as potential drivers of abnormal heart rhythms, for each sensing location at or substantially about said region, determining from predominant activations, an earliest activating electrode site;

for each determined earliest activating electrode site:

calculating a value for each of a plurality of modifiers associated with the electrode site, the modifiers being determined from the electrogram data for the site, tissue characteristics of the site or anatomical characteristics of the site;

determining a ranking factor calculated from the plurality of modifiers;

ranking the each of said earliest activating electrode sites in dependence on its ranking factor; and, outputting data identifying said regions, the data varying prominence of each of the determined earliest activating electrode sites in dependence on said ranking.

The data varying prominence of each of the determined earliest activating electrode sites in dependence on said ranking might suppress display of sites, highlight them in a report/spreadsheet, change visual prominence of a site in a graphical display (which might be overlaid over a view of the heart etc), act as a trigger to a scanning system to consider/ignore the area etc.

The modifiers determined from electrogram data may include:

the minimum cycle length of electrograms recorded at that electrode, the gradient in activation frequency between electrograms recorded at that electrode or within that region and electrograms obtained within a pre-defined geodesic distance, and the average voltage of local electrograms recorded within that region.

A modifier on tissue characteristics may include a measure of presence and density of scar tissue determined by imaging.

A modifier on tissue characteristics may include a measure of tissue impedance at that site.

A modifier may be determined from results of treatment at another earliest activating electrode site.

A modifier on tissue characteristics may be calculated by reference to the results of ablation at similar sites in previous cases.

A modifier on anatomical characteristics may comprise a predetermined weighting factor that depends on the location of the electrode site.

The outputting of data may comprise causing display of the data with a visual indication that varies in prominence for each of the determined earliest activating electrode sites in dependence on said ranking.

The method may further comprise:

determining a predominant electrogram wavefront trajectory for each electrode site;

determining a vector of predominant derived electrogram activations across the multiple electrodes and activations;

classifying an electrode site as being an earliest activating electrode site and potential driver site if the direction of the activation progresses from the electrode site to one or more nearby electrodes sites compared to a potential driver site; and the sequence and timing of activation is within a predetermined biologically plausible manner, with reference to conduction velocities and paths being within plausible activation sequence.

In one embodiment, a site may be classified as an earliest activating electrode site if activation occurs across at least 2 electrodes subtending less than a predefined angle from the vertex subtended by the potential driver site, and at least one electrogram activation is determined as later than the potential driver site within a defined arc of excitable tissue.

The predefined angle may be less than 180 degrees.

The method may further comprise outputting data to a display or medical scanning device to cause display or navigation of chamber geometry and to guide placement of catheters or electrodes for a subsequent electrogram data acquisition.

The method may further comprise identifying a site for subsequent placement of the catheters or electrodes to eliminate or confirm a previously determined first activating electrode or to extend the electrogram data to a previously unscanned or incompletely scanned region.

The method may further comprise identifying the site from the location of first activating sites already identified or from vectors of activation and gradients in signal leading scores.

The method may further comprise receiving electrogram data in substantially real-time and providing an indication as to when sufficient timing of acquisition has been undertaken for the site being scanned.

The step of determining whether sufficient timing of acquisition has been undertaken may comprise determining that an activation pattern of the site being scanned has reached a predetermined level of statistical certainty. For example a 95% chance that this pattern is not random (if the rhythm was very regular this could be reached within seconds).

The step of determining whether sufficient timing of acquisition has been undertaken may comprise one or more of:

counting down a predetermined time period (e.g. 30 seconds by reference to previous cases), acquiring a pre-set number of activation cycles (e.g. 50 activation cycles) on at least a minimum of a pre-set number of electrodes on the roving multipolar mapping catheter, and acquiring a predetermined time or predetermined number of activation cycles where the pattern of activation across multiple electrodes remains within a pattern-matched sequence.

The method may further comprise deriving wavefront directions by determining which electrode in every electrode pair is leading, and processing the wavefront direction to determine if the earliest activating electrode is a true AFD or represents a passively activating site activated from beyond the boundary of measurement.

Advantageously, in embodiments of the present invention, additional information is utilized whereby a ranking of the importance of earliest activating (leading) sites can be performed. Sites acquired at separate time points during a rhythm that is irregular is complex can be compared and used to validate whether they are truly leading. Other characteristics of the electrical activity of areas of atrial tissue may also be used to help indicate areas where ablation will interrupt or slow AF. The incorporation of other measured factors improve the ability to indicate the areas of the heart for which treatment would provide the best effect. Embodiments incorporate factors to modify, weight or further rank signal leading scores resulting from such mapping, in order to improve the selection of areas for ablation, and to indicate the importance of areas for the persistence of arrhythmia. Furthermore, incorporation of such factors can also be used to provide negative weighting, providing an indication that such areas are unlikely to contribute to arrhythmia mechanisms.

According to another aspect of the present invention, there is provided a computer implemented method for analyzing electrograms acquired from the heart to identify one or more regions of the heart responsible for supporting or initiating abnormal heart rhythms, the computer implemented method using electrogram data recorded from a plurality of electrodes on multipolar cardiac catheters obtained from a corresponding series of sensing locations on the heart over a recording time period, the method including the steps of:

defining specific regions within a chamber of the heart as potential drivers of abnormal heart rhythms by analysis of electrical activation sequences, weighting classification of a region as a potential driver according to factors including if:

the direction of the activation generated wavefront is progressing from the potential driver site to one or more nearby electrodes compared to that driver site during the same acquisition;

the sequence and timing of activation is within a biologically plausible manner, with reference to conduction velocities and paths being within plausible activation sequence;

activation occurs across at least 2 electrodes subtending less than a defined angle, for example less than 180 degrees from the vertex subtended by the potential driver site, and at least one electrogram activation is determined as later than the potential driver site within a defined arc of excitable tissue, and a further acquisition performed in an adjacent location subtending the missing arc of the first potential driver site does not fail to confirm a potential driver site at a similar location, and displaying refined potential drivers in a highlighted manner according to the weighting, the display being in relation to a computer representation of the heart chamber.

According to another aspect of the present invention, there is provided a computer system for identifying one or more areas of the heart muscle responsible for supporting or initiating abnormal heart rhythms using electrogram data recorded from a plurality of electrodes on multipolar cardiac catheters obtained from a corresponding series of sensing locations on the heart over a recording time period, the system comprising:

a processor;

a first memory for storing received electrogram data; and a second memory having program code stored therein that when executed by the processor causes the system to:

identify, from the electrograms, regions within a chamber of the heart which have electrical activation sequences which characterize them as potential drivers of abnormal heart rhythms, for each sensing location at or substantially about said region, determining from predominant activations, an earliest activating electrode site;

for each determined earliest activating electrode site:

calculating a value for each of a plurality of modifiers associated with the electrode site, the modifiers being determined from the electrogram data for the site, tissue characteristics of the site or anatomical characteristics of the site;

determine a ranking factor calculated from the plurality of modifiers rank the each of said earliest activating electrode sites in dependence on its ranking factor; and, output data identifying said regions, the data varying prominence of each of the determined earliest activating electrode sites in dependence on said ranking.

The program code when executed by the processor may cause the system to determine the modifiers determined from electrogram data including one or more of:

the minimum cycle length of electrograms recorded at that electrode, the gradient in activation frequency between electrograms recorded at that electrode or within that region and electrograms obtained within a pre-defined geodesic distance, and the average voltage of local electrograms recorded within that region.

The program code when executed by the processor may cause the system to determine the modifiers on tissue characteristics by obtaining a measure of presence and density of scar tissue determined by imaging.

The program code when executed by the processor may cause the system to determine the modifiers on tissue characteristics by obtaining a measure of tissue impedance at that site.

The program code when executed by the processor may cause the system to determine the modifiers on tissue characteristics by obtaining from results of treatment at another earliest activating electrode site.

The program code when executed by the processor may cause the system to determine a modifier on tissue characteristics by accessing data on the results of ablation at similar sites in previous cases.

The program code when executed by the processor may cause the system to determine a modifier by accessing data to obtain a predetermined weighting factor that depends on the location of the electrode site.

The program code when executed by the processor may cause the system to:

determine a predominant electrogram wavefront trajectory for each electrode site;

determining a vector of predominant derived electrogram activations across multiple electrodes and activations;

classify an electrode site as being an earliest activating electrode site and potential driver site if the direction of the activation progresses from the electrode site to one or more electrodes sites nearby to a potential driver site; and the sequence and timing of activation is within a predetermined biologically plausible manner, with reference to conduction velocities and paths being within plausible activation sequence.

The program code when executed by the processor may cause the system to cause output of a visual indication that varies in prominence for each of the determined earliest activating electrode sites in dependence on said ranking.

The program code when executed by the processor may cause the system to cause output of data to a display or medical scanning device to cause display or navigation of chamber geometry and to guide placement of catheters or electrodes for a subsequent electrogram data acquisition.

Embodiments of the present invention seek to provide a system and method that can be used to refine the STAR method and other similar mapping methods based on human data, typically electrogram data acquired during electroanatomic mapping procedures but also imaging data (e.g. tissue characteristic or anatomical data acquired from CT or MRI scanning), to prioritise statistically identified potential AFDs in order of factors that may include:

Measurements of and comparisons between cycle lengths of potential AFDs identified, particularly the shortest cycle length, lowest cycle length variation compared to other identified AFDs, the presence of steep cycle length (CL) gradients around AFDs.

Steepest or presence of CL gradient between the potential AFD and the surrounding electrodes recorded on the same acquisition but only if the direction of STAR map generated wavefront is progressing from the AFD to the electrode paired with (to avoid high cycle lengths associated with collision of wavefronts.

A wavefront is considered as to originate from that AFD site if it seen to propagate across at least 2 electrodes subtending less than 180° from the vertex subtended by the AFD.

Other criteria that may be applied include:

If an AFD has no pairs with electrogram timings later than it within a 180° arc then it is assumed to be a peripheral point with activation potentially arriving from a direction within that 180° arc rather than originating from the AFD with the exception if there is scar within that 180° arc An AFD can only be marked as such if it has more than one electrode pair later than it (and these pairs are widely spaced enough that they do not allow a vacant arc of 180° from the AFD, in which case the AFD is considered a peripheral activation rather than true AFD) The example of 180 degrees is given as this activation site can be indicated as arriving from a direction within that defined arc rather than originating from the potential driver site.

In preferred embodiments, potential AFDs may have their relative importance further refined by reference to specific modifying features derived from the electrogram characteristics or tissue characteristics of underlying tissue.

One embodiment is directed to a system for analyzing electrograms acquired from the heart to define specific regions within a chamber of the heart which have electrical activation sequences which identify them as potential drivers of abnormal heart rhythms, and classify the importance of each of said defined region by characteristics of the electrograms at that region, other than the sequence of activation, anatomical or imaging properties, surface electrograms and/or patient characteristics, which may include:

Shortest or minimum cycle lengths compared to all other early activating sites identified, and/or which may be further refined by only considering a gradient between a potential driver and nearby electrode recorded on the same acquisition if the direction of the calculated activation sequence is progressing from the potential driver to the electrode it is being compared with, and/or the lowest cycle length variability compared to all other early activating sites identified, and/or the steepest or presence of cycle length gradients between one early activating site and one or more electrodes recorded on the same acquisition within a defined geodesic distance (e.g. <3 cm for irregular rhythms) of the potential site of interest; and/or an assessment of geodesic distance of sites of interest from areas with abnormal unipolar and/or bipolar electrogram voltage, and/or an assessment of frequency analyses or gradients of frequency analyses such as dominant frequency at the site of interest and other sites within a defined geodesic distance, and/or and assessment of anatomical and structural features that may be identified with imaging methodologies such as intracardiac echocardiography, cardiac magnetic resonance imaging, cardiac computed tomography, for instance:

Proximity to pulmonary veins or atrial appendage tissue
Junctional of the appendage and veins
Vein of marshall
Mitral valve annulus
Moderator bands
Aneurysm
Identified scar
Variations in tissue thickness
and/or an assessment of tissue electrical impedance, and/or an assessment of tissue movement or thickening, either directly by imaging, or by reference to the movement of cardiac catheters in contact with the cardiac tissue, and/or an assessment of the correlation of identified sites of interest with sites identified as being important by other cardiac rhythm mapping systems, such as to give higher importance to areas of interest identified by two or more methodologies which may be located on the same cardiac geometry or within the same anatomical region on two or more geometries created by different cardiac mapping systems; and apply a weighting to further classify the likelihood of a beneficial effect of intervention at these sites which may be determined by reference to previously acquired data, and the responses to ablation, where a machine learning technique may be used to calculate and optimize the weighting factors to be employed and, display the data with a visual indication of the classification of the calculated importance of these sites.

In one embodiment, a system for analyzing electrograms acquired from the heart is disclosed. The system may define specific regions where electrode activations generally precede the activations of electrodes within a specific geodesic distance and calculate proportions of time or signal leading scores for each identified location and leading scores are modified by applying adjustment factors calculated from other characteristics of electrograms, anatomical or imaging properties, surface electrograms and/or patient characteristics.

The characteristic of averaged wavefront directions or vectors (derived from determining which electrode in every pair is leading i.e. STAR mapping) can be used to confirm if an electrode determined to be a potential AFD is indeed a true AFD. An electrode on the edge of the area being mapped in one acquisition that is determined to be a potential AFD may represent a passively activating site, itself activated from beyond the boundary of measurement. If that potential AFD site is likely to be passively activated, it may have its prominence reduced.

Embodiments can be used both for recorded data (highlighting AFD sites that may be questionable or confirmed). Alternatively, embodiments can operate in substantially real-time, to highlight or instruct the user to move electrode mapping catheters to areas which would most likely overlie AFDs, or instruct them to move away from areas that would be unlikely to overlie AFDs (i.e. an invention of a system that uses these features to direct the movement of the mapping catheter).

In one embodiment, a system for recording and analyzing electrograms acquired from the heart is disclosed. The system may define specific regions within a chamber of the heart which have electrical activation sequences which identify them as potential drivers of abnormal heart rhythms, where apparently potential arrhythmia driver sites acquired with sequential multipolar mapping are further classified by separate rules to determine whether the driver site identified on a single mapping acquisition is a true source of arrhythmia:

where electrode sites are classified as being a potential driver only if the direction of the activation generated wavefront is progressing from the potential driver site to one or more electrodes compared to that driver site during the same acquisition; and where an electrode site is classified as being a potential driver only if the sequence and timing of activation is within a biologically plausible manner, with reference to conduction velocities and paths being within plausible activation sequence and activation across at least 2 electrodes subtending less than a defined angel, for example less than 180 degrees from the vertex subtended by the potential driver site;

and where an electrode site may be excluded as being a potential driver, i.e. classifying it as a passively activating site, if it has no pairs with electrogram timings later than it within a defined arc of excitable tissue, for example 180 degrees (as this activation site can be indicated as arriving from a direction within that defined arc rather than originating from the potential driver site), and where a further acquisition performed in an adjacent location subtending the missing arc of the first potential driver site does not confirm a potential driver site at a similar location, and where identified scar tissue is classified as unexcitable and is considered as not contributing to the arc of activation.

Further amendments and modifications to weighting factors may be made dependent on the characteristics of the electrograms at that region (in addition to the sequence of activation), the anatomy of the potential driver sites, imaging properties around potential driver sites, the characteristics of surface electrograms and/or patient characteristics. Typical electrical characteristics to be taken into account as weighting factors may include:

The shortest or minimum cycle lengths compared to all other early activating sites identified, which may be further refined by only considering a gradient between a potential driver and nearby electrode recorded on the same acquisition if the direction of the calculated activation sequence is progressing from the potential driver to the electrode it is being compared with.

Furthermore, other electrical properties of recorded electrograms at potential driver sites that may be considered relevant and which a quantification of may be used as an input to a modifying factor includes the lowest cycle length variability compared to all other early activating sites identified, and/or the steepest or presence of cycle length gradients between one early activating site and one or more electrodes recorded on the same acquisition within a defined geodesic distance of the potential site of interest; and/or an assessment of geodesic distance of sites of interest from areas with abnormal unipolar and/or bipolar electrogram voltage, and/or an assessment of frequency analyses or gradients of frequency analyses such as dominant frequency at the site of interest and other sites within a defined geodesic distance, and/or a measure of tissue electrical impedance at potential driver sites.

Any one or combination of the above can be used to further determine the likelihood of a specific site contributing to the genesis of an arrhythmia, and straightforward quantification of such sites can be used as a modifying factor.

Furthermore, an assessment of anatomical and structural features may be performed with imaging methodologies such as intracardiac echocardiography, cardiac magnetic resonance imaging or cardiac computed tomography, and one or more resulting quantified metrics used as an input to a modifying factor.

Anatomical locations can themselves be also used with a factor based on the proximity to an anatomical structure, for instance the calculated geodesic distance to any one or more defined anatomical point such as:

Proximity to pulmonary veins or atrial appendage tissue
Junctional of the appendage and veins
Vein of Marshall
Mitral valve annulus
Moderator bands
Aneurysm
Identified scar
Variations in tissue thickness may be used to calculate a modifying factor. Dynamic assessments of tissue movement or thickening, either directly by imaging, or by reference to the movement of cardiac catheters in contact with the cardiac tissue, could refine the importance of sites further by use as a modifying factor.

In one embodiment, a computer implemented method for analyzing recorded electrograms acquired from the heart is operated to identify, from the electrograms regions within a chamber of the heart which have electrical activation sequences which characterize them as potential drivers of abnormal heart rhythms, and ranking the importance of each of said defined region by applying a ranking factor to each identified region, where the ranking factor is a product of a plurality of normalized factors and is subject to a pre-determined weighting factor, including the minimum cycle length of electrograms recorded at that electrode, once extreme outliers have been excluded, and the gradient in activation frequency between electrograms recorded at that electrode or within that region and electrograms obtained within a pre-defined geodesic distance, and the average voltage of local electrograms recorded within that region, and display the data with a visual indication of the classification of the calculated importance of these sites.

In another embodiment, a system for analyzing electrograms acquired from a human or animal heart includes a computer processor configured to execute computer program code to:

identify, from the electrograms, activation sequences of electrical activity to define specific regions within a chamber of the heart which have electrical activation sequences which characterize them as potential drivers of abnormal heart rhythms, and rank the importance of each of said defined region by applying a ranking factor to each identified region, where the ranking factor is a product of a plurality of normalized factors and subject to a pre-determined weighting factor, where the ranking factor is calculated from factors selected from a set including:

the minimum cycle length of electrograms recorded at that electrode, once extreme outliers have been excluded, and the gradient in activation frequency between electrograms recorded at that electrode or within that region and electrograms obtained within a pre-defined geodesic distance, and the average voltage of local electrograms recorded within that region, and the data are displayed with a visual indication of the classification of these sites on a representation of the heart chamber.

More than one cardiac mapping system may be used at once, and a correlation of identified sites of interest with sites identified as being important by other cardiac rhythm mapping systems, can be used as a modifying factor as to give higher importance to areas of interest identified by two or more methodologies which may be located on the same cardiac geometry or within the same anatomical region on two or more geometries created by different cardiac mapping systems.

Each of the defined factors can be subject to a weighting factor, which is designed to provide a measure of the likelihood of a beneficial effect of intervention at such a site. Such weighting factors can be determined by reference to previously acquired data, responses to ablation of previous patients and/or by reference to responses to ablation in the same patient under investigation. Machine learning techniques can be used to calculate and optimize the weighting factors to be employed and the resultant sites displayed with a visual indication of the classification of the final calculated importance of each sites, for example by a color scale, percentage likelihood of arrhythmia termination or beneficial effect, or ranking of importance.

Embodiments of the present invention seek to provide systems and methods for improved analysis of CL, sites demonstrating greater rapidity and organization would improve the sensitivity and specificity of identification of driver sites in AF as identified by methods seeking to identify the areas of the heart where activation precedes adjacent areas. In one embodiment, the STAR mapping method is employed, but other methods whereby potential driver sites may be identified exist. Potential AFDs may be identified by statistical methodologies seeking to identify the earliest local regions of activation, or by other commercial methodologies (such as Cartofinder [Biosense Webster, Haifa, Israel], Acutus, ECGi mapping [e.g. Cardioinsight, Medtronic, Ireland], Ablacon, Topera [Abbott Ltd., Mn, USA]). It will be appreciated that electrogram characteristics that are applicable to the atrium (such as AFDs) may be also applicable to other cardiac rhythms and chambers, such as ventricular fibrillation or tachycardias.

In experimental trials, potential AF drivers (AFDs) have been identified using the STAR method and confirmed AFDs were those potential AFDs that responded to ablation at those sites with either a slowing of AF cycle length of >30 ms or termination of AF. However, it will be appreciated that other factors can also be applied to more accurately identify AF drivers.

Furthermore, testing has shown that the driver sites identified using the STAR approach which demonstrate greater rapidity and organization would be more mechanistically important in maintaining AF as evidenced by a greater likelihood of AF termination with ablation.

There are several novel methods which may be used as weighting factors which may be used in modifying signal leading scores (ranking factors) that may be used in embodiments of the present invention. These may be subdivided into modifiers relating to a single electrode, those related to the relationship between a single electrode and the surrounding electrodes, modifiers relating to non-electrical anatomical or physiologically-derived location-specific and individual patient specific data, location specific modifiers derived from outcome characteristics of patient groups and general modifiers, that may include demographic data.

Embodiments of the present invention include a device and associated computer-implemented method that seek to improves effectiveness of identifying potential arrhythmia driver sites from electroanatomical mapping, allowing them to be better classified and their importance determined. The data produced may be displayed to a physician or otherwise output or passed to other systems. It may be used during a cardiac catheter procedure, such as a catheter ablation procedure (either immediately or at a later sitting) to highlight where ablation will have the most beneficial effect. Such data could be used to enable targeting of non-invasive therapies e.g. radiotherapy, gamma knife, proton-beam treatment.

One potential use of embodiments of the present invention is in the treatment of patients who have been diagnosed with persistent atrial fibrillation, and in whom ablation treatment consisting of pulmonary vein isolation has not resulted in complete cessation of their arrhythmia. In these patients, another mapping process such as STAR mapping may be employed to better target further ablation, and this process would be improved with embodiments of the present invention.

BRIEF DESCRIPTION OF THE DRAWINGS

Embodiments of the present invention will now be described by way of example only with reference to the accompanying drawings in which:

FIGS. 2A-2E are further schematic diagrams showing aspects of determination of a driver site in embodiments of the present invention;

FIGS. 3A-3F are illustrations showing determination and use of maximum spread angles in embodiments of the present invention;

FIGS. 4A-4B are schematic diagrams showing operation of aspects of embodiments of the invention;

DETAILED DESCRIPTION OF DRAWINGS

Figure 1A:
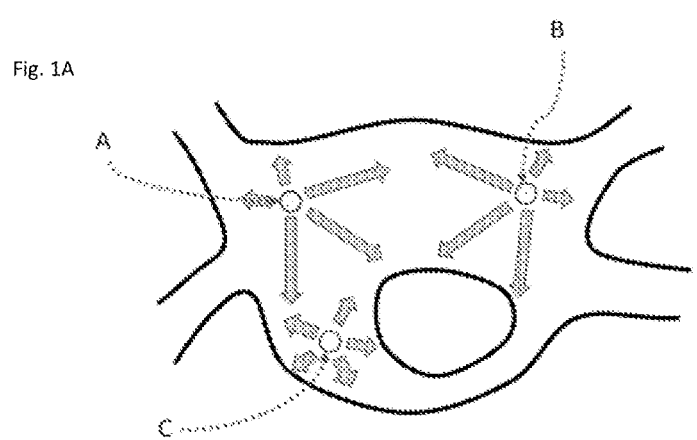
FIGS. 1A-1D are schematic diagrams showing aspects of determination of a driver site in embodiments of the present invention.
Figure 1B:
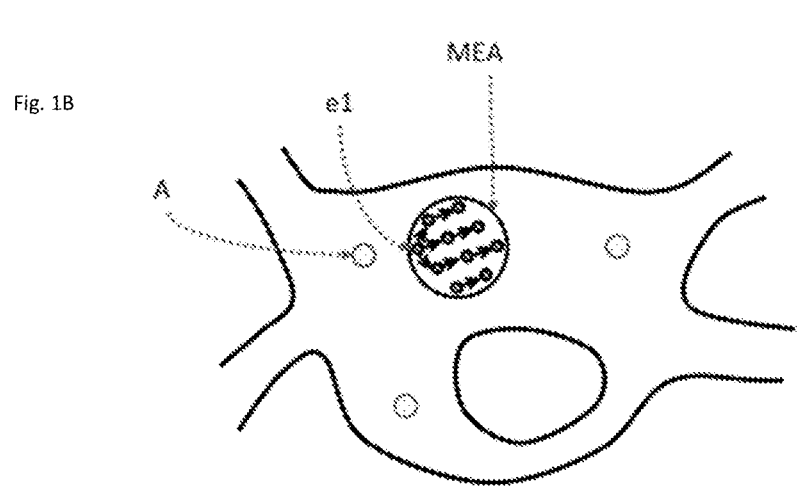
Figure 1C:
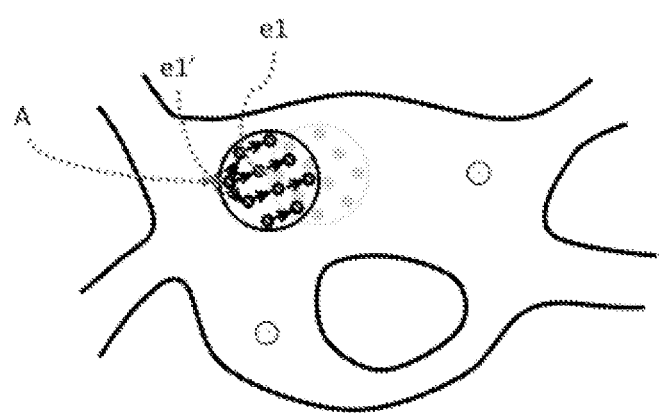
Figure 1D:
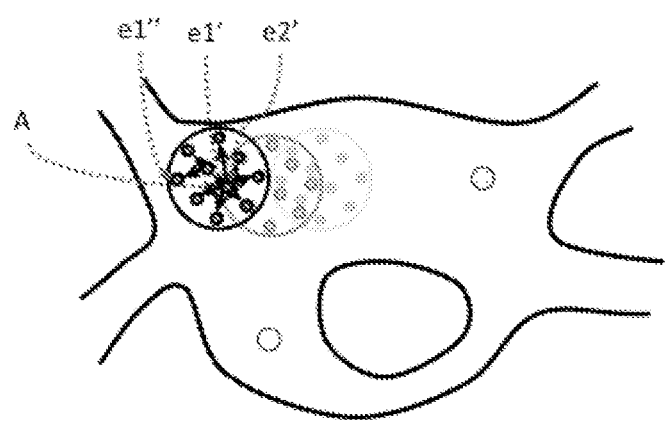

In the embodiments described below, the system may be used in conjunction with whole chamber basket catheters (Constellation catheter, Boston Scientific, ltd, US and FIRMap catheter, Abbott, US) to allow for simultaneous panoramic left atrium (LA) mapping. However, other suitable catheters/electrodes may be used for obtaining electrogram data and it is not necessary to collect data from the whole area of interest simultaneously. The area of interest can, for example, be divided into smaller areas, electrogram data collected sequentially before analysis. The results of the analysis may then being combined and displayed in a single STAR map.

The system used to obtain and process the electrogram data typically includes one or more multipolar electrical catheters (e.g. the basket catheters referred to above, and other intracardiac catheters e.g. a decapolar catheter placed in the coronary sinus) which are inserted into a cardiac chamber of a patient, an amplifier and analogue to digital (AD) converter, a console including a signal analyser, processor and GPU, display unit, control computer unit, system for determining and integrating 3D positional information of electrodes.

The system may use known hardware and software such as the Carto™ system (Biosense Webster, J&J), NavX Precision™ (Abbott Medical) or Rhythmia™ (Boston Scientific) for catheters, 3D electroanatomical integration and processing units. Catheters such as "basket" catheters, circular or multi-spline mapping catheters (e.g. Lasso catheter, Biosense Webster, J&J, HD-mapping catheter, Abbott Medical SJM, Pentarray Biosense Webster, J&J), decapolar catheters or ablation catheters may be used. These systems and catheters are used to gather electrogram signals and corresponding location and time data pertaining to electrical activity at different locations within the heart chamber. These data are passed to a processing unit which performs algorithmic calculations on these data and aims to translate these data to provide location information to the physician on the areas within the heart which are most likely to be responsible for the maintenance and persistence of abnormal heart rhythms. Alternatively, the system may use bespoke catheters, tracking systems, signal amplifiers, control units, computation systems and displays.

In the above identified patent applications, a mapping system, referred to in the following as the "stochastic trajectory analysis of ranked signals (STAR) mapping" system, is described. It has the aim of identifying sites of drivers of cardiac arrhythmias, which can for example be displayed in the form of a 3D map. Maps created using the STAR-mapping system are referred to as "STAR maps".

When performing star mapping (and also acquiring data for embodiments of the present invention), a physician may place a multipolar panoramic mapping catheter in the lateral left atrium, acquire data for a period of time (e.g. 5 seconds to 5 minutes), then reposition the catheter to ensure close apposition to the left atrial septum or anterior wall and another recording performed. It will be appreciated that this could be performed ahead of time and the processing performed on pre-recorded data.

Proportions of "leading" electrode will be coherent between maps, therefore data and proportions would be able to be displayed on the same map without problem. In this way, multiple coherent statistical maps may be built up sequentially by moving catheters within the chamber and taking further recordings.

The following are main steps in the process that is used to identify "leading" signals (that are indicative of areas/sites in the heart that are statistically likely to be driving abnormal heart rhythms, following acquisition of the electrogram data (along with corresponding spatial and temporal data).

First, interference and far-field signal components are removed from input electrogram signals. In one embodiment, the system breaks down signals into relevant components e.g. by spectral analysis, far-field signal blanking, far-field signal subtraction, filtering or by another method known in the art. Signal components originating within the chamber of interest in the heart (e.g. atrial signals) are identified. Relative timings of atrial signals are established, which may be in an explicit, stochastic or probabilistic manner. In some embodiments, the phase of each signal may be determined and relative timings established from relative phase shifts between different electrodes.

Second, signal timings from adjacent electrodes are paired. Signals are only paired with one another if electrode locations are within a specified geodesic distance from one another i.e. only electrodes close to each other are paired to each other. This may be further improved by only pairing electrodes that are located on the same aspect of the chamber wall; i.e. adjacent electrodes on the back wall of the heart will be considered adjacent but not if the electrodes are on opposite sides of a discontinuity, e.g. a pulmonary vein, even though the absolute distance between such electrodes may be small. Relative timings of activation at paired electrodes is thus established, with a value to a "leading" electrode ascribed. This pairing may be carried out for discrete analysis time periods, typically of between 10 ms and 200 ms in duration. The length of the analysis time periods need not be constant across all of the data being analysed. The aim is to compare timings between activation of paired electrodes caused by the same activation sequence and the analysis time periods can be determined accordingly. For example, each analysis time period can be chosen to encompass electrode activations that are likely to have resulted from the same activation sequence. Accordingly, analysis time periods may overlap one another.

Third, this process is repeated many times (i.e. for many analysis time periods, for each pairing) over a given period of time. Advantageously, the analysis time period overlaps, and is shifted in relation to the initial analysis time period for example 10 to 120 seconds. Within the given period of time, the analysis time periods may overlap, as noted above. For example, if the analysis time period is 200 ms, the analysis time periods may overlap by 100 ms, i.e. 50%. In other words, the leading electrodes are determined for a first 200 ms period, then for a second 200 ms time period, the second time period starting 100 ms after the start of the first time period, and so on, for the given period of time. As with the analysis time periods themselves, the degree of overlap may vary over the data set. By such repetitive analysis it is possible to discard activation sequences that repeat less frequently or not at all and rank activations sequences that appear more frequently with more importance and priority.

In atrial fibrillation the activation patterns appear chaotic with frequent changes in wavefront propagation. The relative proportions of 'time' that each site precedes each of its neighbors in the activations mapped is calculated, and thus a proportional map of the more frequently "leading" electrode sites is created.

Fourth, proportions of 'time' that each recorded area spends "leading" activations are calculated. This calculation may be based on actual duration of time during which each electrode is judged to be leading its paired electrodes. Alternatively, it may be the proportion of total analysis time periods (whether those time periods are of the same or different durations to one another) for which the site leads in mapped activations. Thus, in some examples, the relative proportions are in effect determined by looking at the total number of atrial activation signals seen by a given electrode and determining the proportion of those activation signals for which the electrode is leading relative to a plurality of other electrodes paired with one another. Although mapping only adjacent electrodes may give rise to errors, the system maps all electrodes relative to all others for each cycle of activation to establish within the mapped field the direction of activation. Sequences are analysed to identify dominant activation sequence during the recording period and the sites that are leading those activations, i.e. the point from which the activations emanate. Activation sequences with a trajectory suggesting a localised source, an AFD, are presumed to be mechanistically important. The STAR mapping system calculates the proportion of activation sequences with a given vector to establish the dominant vector (if any) and the proportion of the time that activations follow that vector. For all sites within the mapping field the proportion of mapped activations originating from that site is calculated to determine its relative importance. These proportions can be termed "leading signal score" and allow for further modification, comparisons and calculation.

The leading signal score is normalised so that proportions may be compared across the heart. Many embodiments of the statistical processes, normalisation and subsequent display of this data can be envisaged.

Electrodes which are overlying completely passive areas of cardiac activation will tend towards having few if any activations appearing to emanate from these. Only activation sites that tend to be frequently "leading" within activation sequences will be ascribed values indicating a high likelihood of being a source of activation. Similarly when considering overlapping electrode sampling locations A and B with activation repeatedly earliest at the edge of the sample A, activation may be seen progressing from B to A and thus the sites of early activation of A may be regarded as passive and electrodes from sample B being regarded as leading, thus greater emphasis be given to leading electrodes from sample B.

This process may be repeated over multiple recording time periods and locations in order to further refine and define patterns of activation that repeat and discard those that do not, thus building up a wider area of mapping than might be achieved from a single activation recording from a multipolar electrode catheter.

The STAR mapping method can be used in embodiments to identify, for regions within a chamber of the heart which have electrical activation sequences which characterise them as potential drivers of abnormal heart rhythms, the predominantly earliest activating electrode site. Alternatively, a method such as the CARTOFINDER™ module running on the Carto™ system (Biosense Webster, J&J) can be used to indicate proportions of time in which an electrode location is preceding the activation of its neighbours. This information can be normalised to form a signal leading score which can be used in the described method to provide improved information as to the importance of such sites.

In one embodiment, a computer implemented method is used to identify one or more regions of the heart responsible for supporting or initiating abnormal heart rhythms. The computer implemented method using electrogram data recorded from a plurality of electrodes of a multielectrode array on multipolar cardiac catheters obtained from a corresponding series of sensing locations on the heart over a recording time period. The method including the steps of: identifying, from the electrograms, regions within a chamber of the heart which have electrical activation sequences which characterise them as potential drivers of abnormal heart rhythms, for each sensing location at or substantially about said region, determining the predominantly earliest activating electrode site for each determined earliest activating electrode site:

calculating a value for each of a plurality of modifiers associated with the electrode site, the modifiers being determined from the electrogram data for the site, tissue characteristics of the site or anatomical characteristics of the site;

determining a ranking factor calculated from the plurality of modifiers ranking the each of said earliest activating electrode sites in dependence on its ranking factor; and, outputting data identifying said regions, the data varying prominence of each of the determined earliest activating electrode sites in dependence on said ranking. This is discussed in the examples below.

FIGS. 1A-D are schematic diagrams showing aspects of determination of a driver site (earliest activating electrode site corresponding to a potential driver of abnormal heart rhythms).

FIG. 1A shows a schematic diagram of an atrium of a human heart. The diagram shows 3 sites of activation driving atrial fibrillation, represented by circles A, B and C. These may be identified as driver sites by several methods, such as Stochiastic Trajectory Analysis of Ranked signals (STAR mapping). In sequential mapping of arrhythmia wavefronts, electrogram wavefront trajectories are determined by using a multielectrode array, represented by the large circle MEA enclosing many individual electrode sites including the electrode e1. The vector of derived electrogram activations is derived across the MEA, here represented by the arrowheaded lines. In this example, the earliest activating site is determined to be e1. When the MEA is moved to a new position, shown in figure panel 1C, electrode sites overlying the original site e1 no longer appear to be leading sites representing characteristics of a driver site, with electrode site e1' actually generally leading in activation.

In embodiments of the present invention, when the electrode sites on the edge of an electrode array acquisition appear to be leading in one acquisition but are not leading in another acquisition that overlaps the leading site in the first acquisition, that site is classified as a driver.

Now consider the site e1', which is leading the acquisition represented in figure panel 1C, and is actually overlying a real driver site, (site A in FIG. 1A). Here, a third acquisition is performed represented in panel FIG. 1D, but on this occasion electrodes (e2") overlying the site e1' continue to have characteristics of signal leading electrodes, whereas the edge electrode site e1" is now moved to a following area. The system confirms the driver site at the site of e1' (and e2") is now positively a driver site.

In this manner sequential acquisitions of electrograms performed around the heart chamber can be used to distinguish true driver sites from apparent driver sites being activated passively by conduction from remote driver sites.

Those practiced in the art will consider that it is possible to perform such sequential mapping and determination of driver sites once all sites have been mapped, dynamically during mapping, or any intermediate point. For example, a map may be produced from acquired data, sites of potential driver sites determined, and potential driver sites that require further mapping or electrogram acquisition in the area to positively classify as a potential driver (or not) can be highlighted in the map to the user or physician. It may be envisaged that such a system be employed to direct a robotically controlled catheter to map towards and around a potential driver site.

FIG. 2A is an illustration of a cardiac chamber (here a schematic of a left atrium) with two independent driver sites represented by stars A1 and A2. The general vectors of cardiac activation wavefronts are shown by the hatched arrows.

Figure 2B:
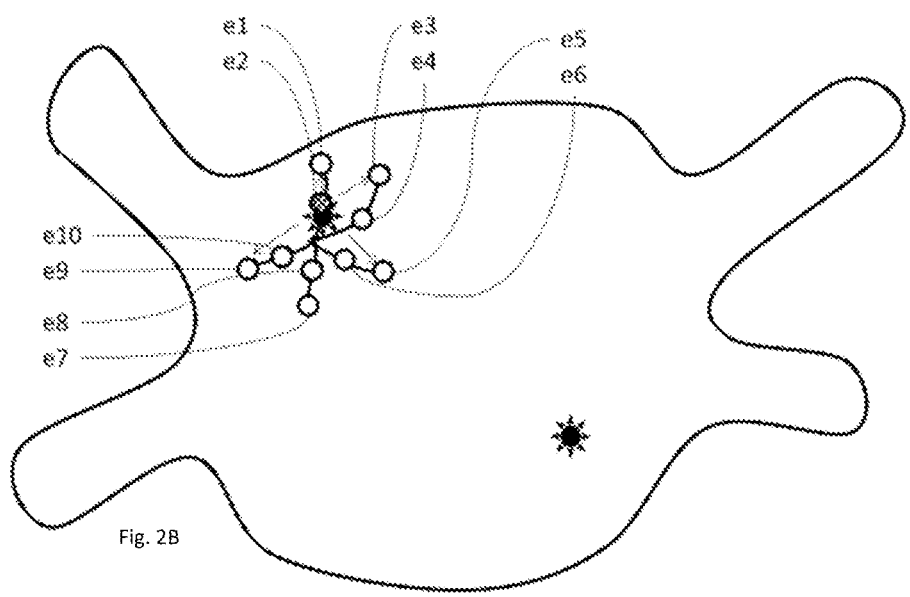

In an embodiment of the present invention, as shown in FIG. 2B, a multipolar mapping catheter, with electrodes e1 to e10 is placed over the A1 AF driver. Electrode e2 is activated earliest, with vectors of activation generally acting away from this site. Resultant displayed vectors are all towards the e2 electrode (arrows from e2, e3, e5 and e9 only shown for clarity) which has the highest leading signal score. As a result, e2 is highlighted to the user.

Figure 2C:
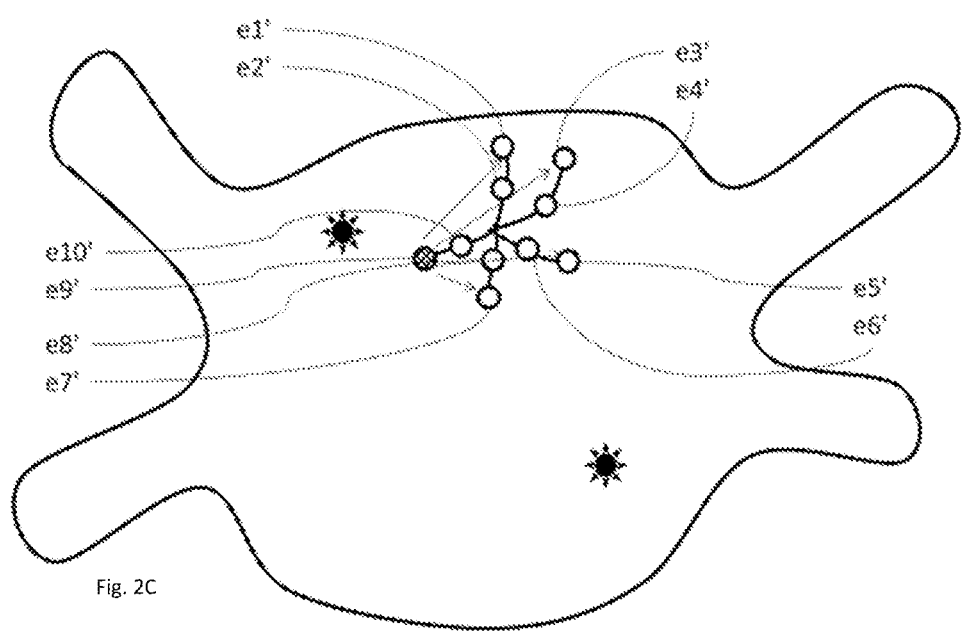

As shown in FIG. 2C, the multipolar mapping catheter is then moved to a site distant from both activation sources. The "leading signal score" will now be highest on the peripheral electrode e9'. Activation is generally in a single direction, generally the peripheral electrode e9' is leading all others.

Figure 2D:
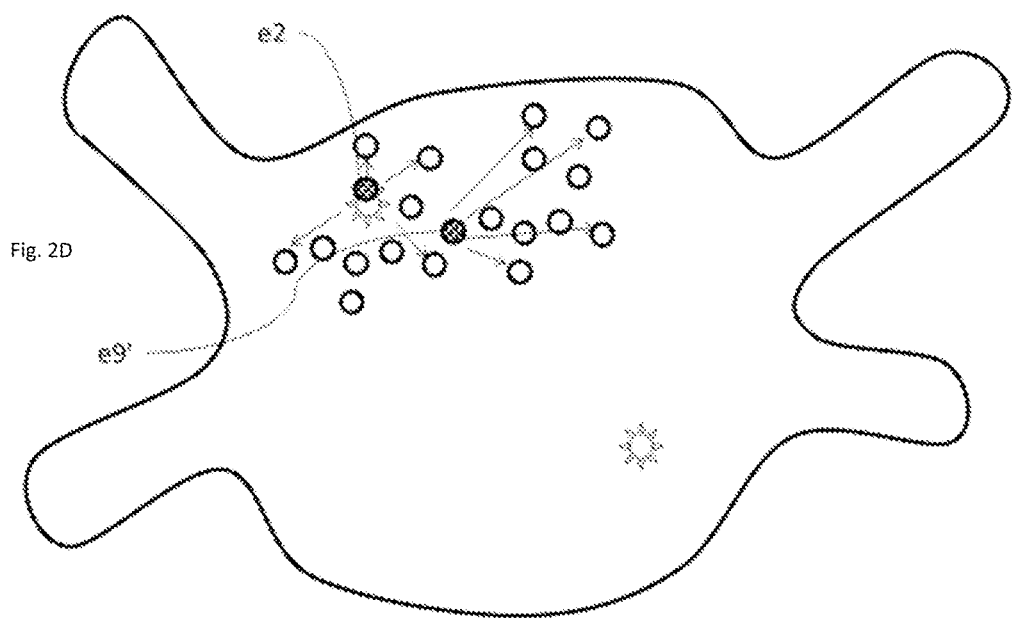

FIG. 2D shows a simplified concatenated map as would be seen in STAR mapping, where electrodes with the highest signal leading scores from each sequential acquisition are highlighted. The two sites representing AFDs are shows now as outlined rather than solid shapes. In this example two electrodes e2 and e9' are highlighted. It is apparent that although electrode e9' is ascribed a high leading signal score, this does not indicate that this electrode indicates a true position of an AFD, unlike e2. The described invention modifies the display of such a site by identifying it either in terms of the resultant vectors towards a site on the periphery of an acquisition, with an adjacent acquisition's activation sequences being concordant (i.e. in roughly the same direction/away from site e9'). Experimental observations also show that such sites exhibit differences in other metrics, such as activation frequency, electrogram voltage and dominant frequency when compared to true AFDs.

In FIG. 2E, the resultant map produced by an embodiment is shown, with e9' having been identified as unlikely to be an AFD site despite the apparently high signal leading score. The visualization of the electrode is therefore modified, by reducing projected size, reducing color highlight or similar. Site e2 can be highlighted further by increasing color intensity, size or other visual modification.

In preferred embodiments, a graphical representation of the map of driver sites is displayed on a display unit.

In one embodiment, identified potential AFDs may have their relative importance further refined by reference to specific modifying features derived from the electrogram characteristics, tissue characteristics or other criteria (e.g. anatomical) of underlying tissue.

In this embodiment, electrogram acquisitions are taken sequentially in groups ($g^{1-}$ etc. through $g^x$) at different electrode sites throughout a cardiac chamber. For example, the electrodes ($e^1$ through $e^{20}$) on a pentarray mapping catheter may be moved to different sites within the left atrium of a patient with atrial fibrillation and different sequential acquisitions of electrograms taken at each site.

From each sequentially acquired electrogram dataset, a signal leading score is calculated for each electrode within a group. This may be by for example by the STAR method or another statistically-based method indicating the proportion of time that activations seen on that electrode precede activations detected by other electrode sites within the simultaneous acquisition.

Alternatively, other methods may provide the proportion of activations in which activation precedes other sites, or the proportion of electrodes within an acquisition that that specific electrode is seen to lead, or a hybrid metric.

Consider a situation with 5 electrodes (e1-e5) on a single group acquisition (g1):

| Sequential Acquisition | Electrode | Signal leading score | Normalised Signal Leading Score |
|---|---|---|---|
| g1 | e1 | 0.3 | 0.21 |
| g1 | e2 | 0.2 | 0.14 |
| g1 | e3 | 1.4 | 1.00 |
| g1 | e4 | 0.7 | 0.50 |
| g1 | e5 | 0.9 | 0.64 |

For each of these sites, one or more further factors may be calculated, for example cycle length variation or minimum average cycle length at each electrode.

Cycle length metrics are calculated by initially identifying all activations on each electrode in an acquisition.

For the calculation of the minimum stable cycle length (Min-CL), the initial activation-to-activation coupling intervals are filtered to remove any activations more rapid or slower than a set point around an average cycle length. For example, activations faster or slower than 30% than the mean CL are disregarded. The shortest of the remaining cycle lengths may represent unstable activations, thus the shortest 10% of activations are excluded. The assigned value for Min-CL is the minimum of the remaining values, equivalent to the shortest cycle length in the $9^{th}$ decile of ranked activation intervals, where the longest cycle lengths are in the first decile and so on.

Each electrode site for each sequential acquisition (here g1-g3) has a value for Min-CL (in ms) calculated. e.g.

| Sequential Acquisition | Electrode | Signal leading score | Normalised Signal Leading Score | Min-CL (ms) |
|---|---|---|---|---|
| g1 | e1 | 0.3 | 0.21 | 177 |
| g1 | e2 | 0.2 | 0.14 | 182 |
| g1 | e3 | 1.4 | 1.00 | 169 |
| g1 | e4 | 0.7 | 0.50 | 165 |
| g1 | e5 | 0.9 | 0.64 | 179 |
| g2 | e1 | −0.2 | −0.13 | 198 |
| g2 | e2 | 0.2 | 0.13 | 187 |
| g2 | e3 | 0.3 | 0.19 | 201 |
| g2 | e4 | 0.7 | 0.44 | 200 |
| g2 | e5 | 1.6 | 1.00 | 187 |
| g3 | e1 | −0.2 | −0.10 | 171 |
| g3 | e2 | 0.5 | 0.24 | 172 |
| g3 | e3 | 0.2 | 0.10 | 182 |
| g3 | e4 | 0.7 | 0.33 | 187 |
| g3 | e5 | 2.1 | 1.00 | 171 |

A min-max feature scaling normalization can be performed across all sites, allowing comparison of min-CL between separate acquisitions. In the case of the modifying variable Min-CL, this normalization is performed to the range of values acquired. In this example, the absolute value of Min-CL subtracted from the maximum value of all Min-CLs across all electrodes and acquisitions is normalized to the variation in this value.

e.g. for g2e2, abs(187 ms-201 ms)=14 ms;

and variation in CL=36 ms;

so $$\text{normalized min-}CL \text{ for } g2e2 = 14/36 = 0.39$$

This value can be multiplied by the original signal leading score for that electrode (here 0.2) to give a modified signal leading score i.e.

$$0.2*0.39=0.05$$

All modified signal leading scores may be normalized once again at this point.

| Sequential Acquisition | Electrode | Signal leading score | Normalised Signal Leading Score | Min-CL | Norm. Min-CL | Modified Signal Leading Score | Normalised, Modified Signal Leading Score |
|---|---|---|---|---|---|---|---|
| g1 | e1 | 0.3 | 0.21 | 177 | 0.67 | 0.14 | 0.16 |
| g1 | e2 | 0.2 | 0.14 | 182 | 0.53 | 0.08 | 0.08 |
| g1 | e3 | 1.4 | 1.00 | 169 | 0.89 | 0.89 | 1.00 |
| g1 | e4 | 0.7 | 0.50 | 165 | 1.00 | 0.50 | 0.56 |
| g1 | e5 | 0.9 | 0.64 | 179 | 0.61 | 0.39 | 0.44 |
| g2 | e1 | −0.2 | −0.13 | 198 | 0.08 | −0.01 | −0.01 |
| g2 | e2 | 0.2 | 0.13 | 187 | 0.39 | 0.05 | 0.05 |
| g2 | e3 | 0.3 | 0.19 | 201 | 0.00 | 0.00 | 0.00 |
| g2 | e4 | 0.7 | 0.44 | 200 | 0.03 | 0.01 | 0.01 |
| g2 | e5 | 1.6 | 1.00 | 187 | 0.39 | 0.39 | 0.44 |
| g3 | e1 | −0.2 | −0.10 | 171 | 0.83 | −0.08 | −0.09 |
| g3 | e2 | 0.5 | 0.24 | 172 | 0.81 | 0.19 | 0.22 |
| g3 | e3 | 0.2 | 0.10 | 182 | 0.53 | 0.05 | 0.06 |
| g3 | e4 | 0.7 | 0.33 | 187 | 0.39 | 0.13 | 0.15 |
| g3 | e5 | 2.1 | 1.00 | 171 | 0.83 | 0.83 | 0.94 |

In this example, site g1e3 and g3e5 would be the two highest scoring sites. Site g2e5 in contrast has its leading score reduced as values for min-CL here were very much higher than in other sites.

A weighting may be used for each modifying variable, which can be applied prior to normalization.

As can be appreciated, this method of providing weighting to electrode leading signal scores, derived from STAR mapping or other electroanatomic mapping methods, can be applied to other electrophysiological phenomena such as cycle length variation, bipolar or unipolar voltage signals at the site, electrogram duration, or stability of activation of other electrodes (i.e. low CL variability on other electrodes).

Further modifying variables may be applied from look-up tables, for example relating to anatomical sites which themselves may be manually or automatically labelled. Alternatively, they may be calculated from anatomic or tissue measures derived from e.g. MRI or CT scans.

The geometric sites corresponding to the locations from which the highest ranking, normalized modified signal leading score sites were acquired are preferably highlighted, for example by increasing or changing the size, opacity, color or marker of those sites or areas on the surface of the rendered cardiac chamber in an output of the data or visual rendering on a display.

In a preferred embodiment that may be used in addition to or as an alternative to that set out above, determination whether a potential AFD is really a true AFD may be made by reference to vectors of activation determined by e.g. STAR mapping.

As before, electrograms are preferably acquired by taking them sequentially in groups (g$^1$ etc. through g$^x$) at different electrode sites throughout a cardiac chamber. For each simultaneous group acquisition of electrograms, approximate vectors of activation are derived by reference to signal leading scores (unmodified) or from other methods (e.g. wavefront direction calculation). An electrode with a high signal leading score which is surrounded by electrodes with lower signal leading scores is likely to represent the site of a true AFD. However, an electrode on the periphery of the geometry of an acquisition with a high signal leading score may either represent a true AFD or be merely a passively activated site that is the nearest to an AFD of in that specific acquisition. It is advantageous to automatically indicate if an acquisition is likely to be a passively activating site.

To determine if a leading electrode site (e.g. e1) on an acquisition may be a true AFD, the electrode with the highest signal leading score in that group acquisition is identified. A tangent plane to the geometrical surface of the chamber is created at a midpoint of the electrogram acquisition site. It is advantageous to use a highly smoothed geometrical representation of the chamber to prevent internalization of the plane. The in-plane angular distributions from an arbitrary bisection of e1 are then calculated, and the in-plane angular distribution of electrodes around that point is determined (spread angles). A lack of angular separations between surrounding electrodes of greater than a predetermined angle (e.g. 120°) indicates e1 is likely to be a true AFD.

A modifying factor can therefore be applied to leading electrode sites identified as AFDs as a determined by a look-up table or as a preselected value. Alternatively, the largest angular separation between electrodes on the acquisition can be inversely rescaled (1-(min-max Normalization)), and this used as the modifying variable.

For example, consider a situation where e2 is surrounded by 4 electrodes on acquisition g1, and the sequential angular separation of these electrodes is 93°, 65°, 119° and 83°. The maximum angle for this example acquisition is thus 119°. A maximal spread angle for an acquisition of e.g. >170° would imply the potential AFD site is on the edge of its group of electrodes.

In this example, three further sites of acquisition, g2 through g4, provide the maximum angles of separation for each acquisition to be 174°, 120° and 240°.

These angles can undergo a normalization, to provide a modifying factor that may be applied with weighting to each of the most likely AFDs seen at each acquisition. In this example 1, 0.55, 0.99 and 0 may arise from a standard max-min normalization. Using maximum possible separation (360°) rather than the measured maximum angular separation provides non-zero normalized modifying factors, in this example: 1, 0.77, 0.99 and 0.49.

In a case where the maximal spread angle of a potential AFD site is greater than 170°, a determination must be made whether this site is passively activating. This can be performed by reference to other acquisitions that have taken place within a prespecified geodesic distance of the potential AFD and are within the arc of the maximal spread angle.

Determining Passive Activation

An electrode that is potentially an AFD site that is on the perimeter of a simultaneous acquisition can be classified into a likely true AFD or a passively activating site by reference to the activation sequences or average wavefront vectors of separate acquisitions close to that site which give coverage within the maximal spread angle arc. These are preferentially within a certain geodesic distance from the AFD site in question, typically within a predefined distance e.g. within 3 cms.

For example, an electrode acquisition g1e1 is on the periphery of an acquisition and is identified as a potential AFD. A further acquisition, g2, within 3 cms and within the arc of the maximal spread angle, is performed and calculation applied. If g1e1 is passively activating, the nearest electrode signal leading scores on g2 will be expected to be low. This may be defined as the signal leading scores on the one (or more) nearest electrodes of g2 (e.g. g2e1) being in the lower 50% of all the signal leading scores for g2. Further, the vectors of activation of such electrodes will be directed away from g1e1, i.e. lie between for example 90° and 270° on a planar tangent, where vector from g2e1 to g1e1 is taken as 0°.

If both these conditions are fulfilled, g1e1 may be defined as a definitely passively activating site. To thus modify by reduction the prominence of g1e1 in calculations, a modifying factor may be applied reducing its signal leading score. This modifying factor may be arbitrary from a look up table or from prior investigation and may be applied either to the single electrode site (g1e1) or across all electrodes within the sequential acquisition (e.g. g1).

An iterative process may be then performed, where signal leading scores are recalculated following reassignment and normalization of signal leading scores.

If however g2e1 and/or its neighbors signal leading scores are high (e.g. within the top 75% of leading signal scores for activation g2), and the vectors of activation are towards the site g1e1 (e.g. between −90° and +90° on the planar tangent interelectrode vector), a true AFD driver is likely at or very close to these two electrode sites. A positive modifying factor may be applied, and the area between g2e1 and g1e1 may be highlighted visually.

There may be a situation where an electrode with a high signal leading score is on the edge of an acquisition and there is no acquisition within both the arc of the maximal spread angle and the defined geodesic distance. In this case, the area can be highlighted on a display screen to indicate that a further acquisition in that area should be taken. This could be either by highlighting the area with a different color or by indicating with an arrow, pointer or other animation that a further acquisition should be performed.

During such an acquisition an indicator may be displayed showing whether sufficient electrogram data had been acquired. At its simplest, this may be a simple timer, but other indicators may count numbers of electrogram activations on each electrode, with a target number preset by reference to a predetermined value.

FIGS. 3A-3F are illustrations showing determination and use of maximum spread angles in embodiments of the present invention.

Figure 3A:
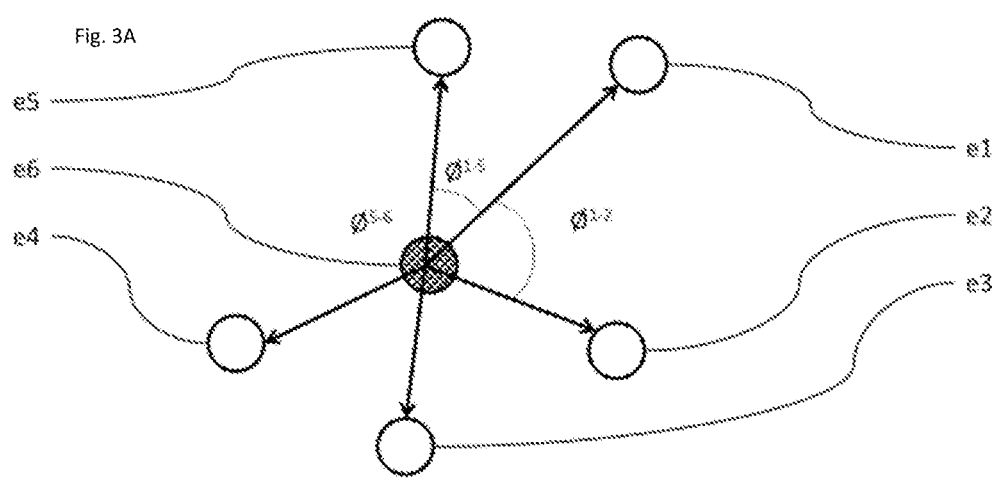

FIG. 3A shows a multipolar mapping catheter with 6 electrodes labelled e1 to e6. In this example electrode e6 has a higher signal leading score than other electrodes. Vectors of activation between this electrode and surrounding electrodes are drawn by the solid arrows, these are projected on a tangential plane to a smoothed cardiac chamber surface representation at e6. An angle exists between these vectors, for example the two vectors from e6 to e1 and from e6 to e5, angles here are given by ø1-5. In this example, e6 is surrounded by electrodes, the largest angle ø5-6, which can be termed the maximal spread angle, is smaller than a preset maximum e.g. 120°. This confirms e6 as an AFD and a modifying factor can therefore be applied.

Figure 3B:
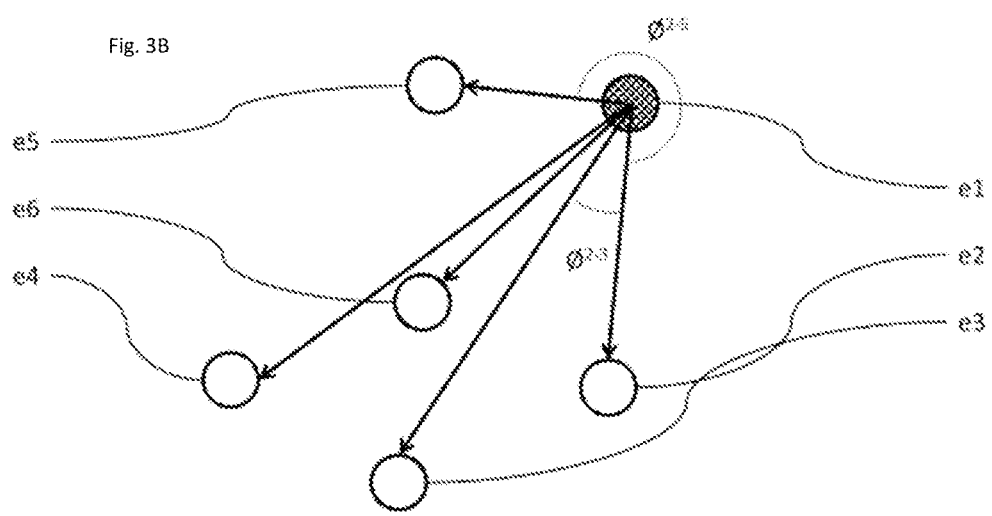

FIG. 3B now shows the same arrangement of electrodes moved to another location. Here the potential AFD, i.e. the electrode with the highest signal leading score, is e1. However, in this example the largest interelectrode angle is now ø2-5, which is greater than a set amount (e.g.) 170°, confirming this as a peripheral point on the activation.

Figure 3C:
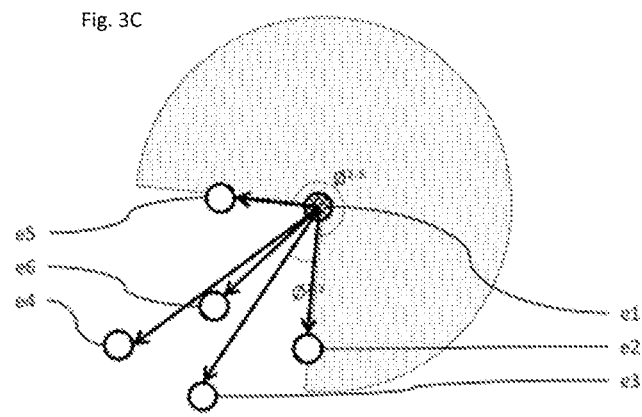

FIG. 3C illustrates an arc of a set diameter (e.g. 3 cm) and centered on the maximum spread angle (in this example ø2-5) may be considered, shown by the shaded area. This may completely cover the angle ø2-5 or may be smaller and centered upon it. The nearest two or more electrode activations from separate grouped acquisitions lying within this arc are then considered.

As shows in FIG. 3D, the nearest two or more electrode activations from separate grouped acquisitions (g2e1-g2e6) lying within this arc are then considered. In this example, the nearest two acquisitions g2e4 and g2e3 both have low signal leading scores and are not potential AFDs. Further, the average vector of activation, shown by the bold solid arrow is towards e1 (rather than away e1, as would be expected if e1 was a true AFD). This confirms e1 in this example as not an AFD, and a modification factor may be applied to it to reduce its visual prominence.

Figure 3E:
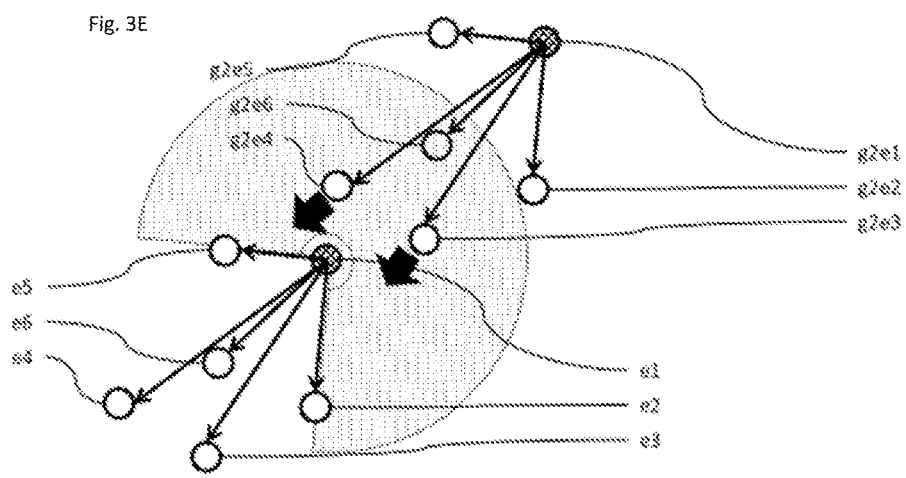
Figure 3F:
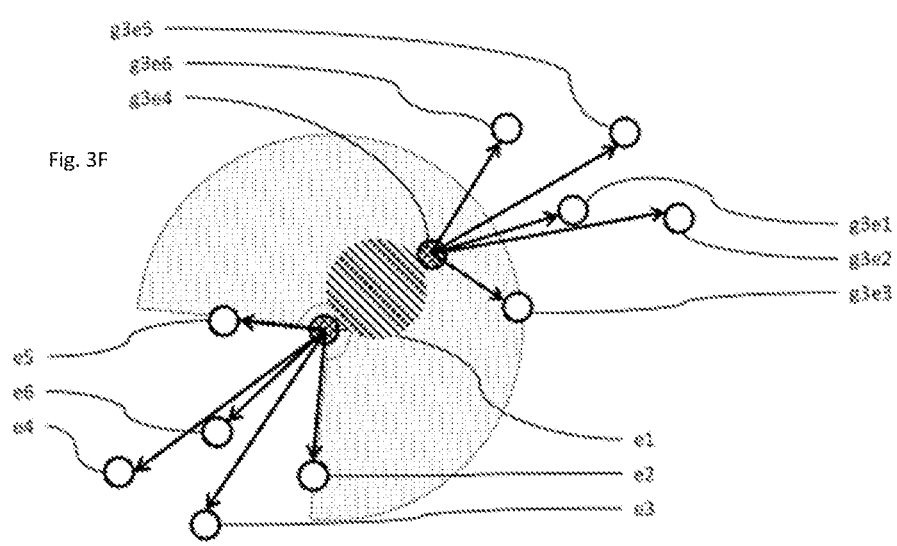

FIG. 3E shows another situation where one of the closest electrode on a further acquisition (g3e4) has a high signal leading score, and vectors from this electrode are in the opposite direction to those from e1. This indicates that an AFD does exist near to these two electrodes and the area between them may be highlighted (e.g. here with a striped circle).

Figure 4B:
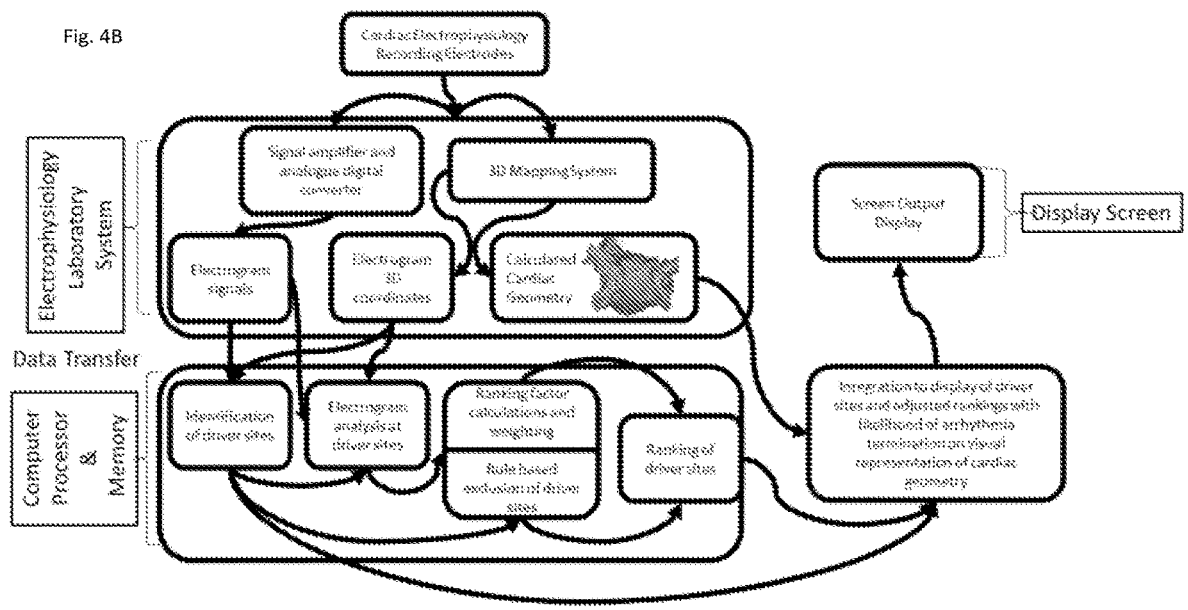

FIGS. 4A and 4B illustrate how data from other electrogram analyses or from imaging technologies may be used in combination with areas identified by mapping of electrogram vectors to better classify and rank the importance of identified areas. In this example, areas A B and C are first identified using a mapping technology, for example STAR mapping; further datasets which can indicate the likelihood of areas being important for the maintenance of the heart arrhythmia can be combined and used to rank the identified driver sites. One method for doing this is to use areas to provide a normalised modifying factor which is then applied to the corresponding driver sites. Several modifying factors may be applied to each identified driver site to give a final probable ranking or display of respective importance of all driver sites identified by the original mapping method. Further data such as from historic patient data may be applied, and machine learning algorithms used to determining the exact modifying factors to use and the order in which to apply them.

As illustrated in FIG. 4A, data acquired from electroanatomic mapping can be both used for determining potential driver sites by activation sequence mapping e.g. STAR mapping and also used for analysis of other electrical properties at these sites (i.e. analysis of electrogram characteristics in these regions). A further rule-based approach, as detailed in FIG. 1, may be employed if mapping has occurred sequentially in order to remove driver sites which are in fact passively activating. These resulting data can be further combined with other information regarding that patient's heart which is under investigation e.g. imaging derived metrics, by virtue of this imaging data would give rise to a modifying factor which can be normalised, weighted and used to modify the importance ascribed to each driver site identified. Such data might be cardiac MRI data containing a percentage scar, wall thickness or tissue oedema measure for example, which itself may consist of a scale of enhancement with a contrast agent e.g. late gadolinium enhancement. Another source of modifying information may be by reference to historic data, which may be coupled to machine learning techniques to further derive modifying factors for each identified potential driver site.

FIG. 4B illustrates the flow of data through a proposed device. Electrogram data are acquired with multipolar mapping catheters connected to a cardiac mapping system, which may be incorporated into or separate to a 3D electroanatomic mapping system. It will be appreciated that rather than intracardiac catheters being used to collect data on cardiac electrograms, surface electrograms may be employed via the inverse solution to derive "virtual" electrograms on a representation of the cardiac chamber surface. Data is then transferred to an analysis module, which may exist as a separate computer or be integrated to the electro-anatomic mapping system. Here, the data integration and processing described in FIG. 4A is performed, before integration with a 3D anatomical representation of the heart and display to the user, e.g. a physician.

Figure 5A:
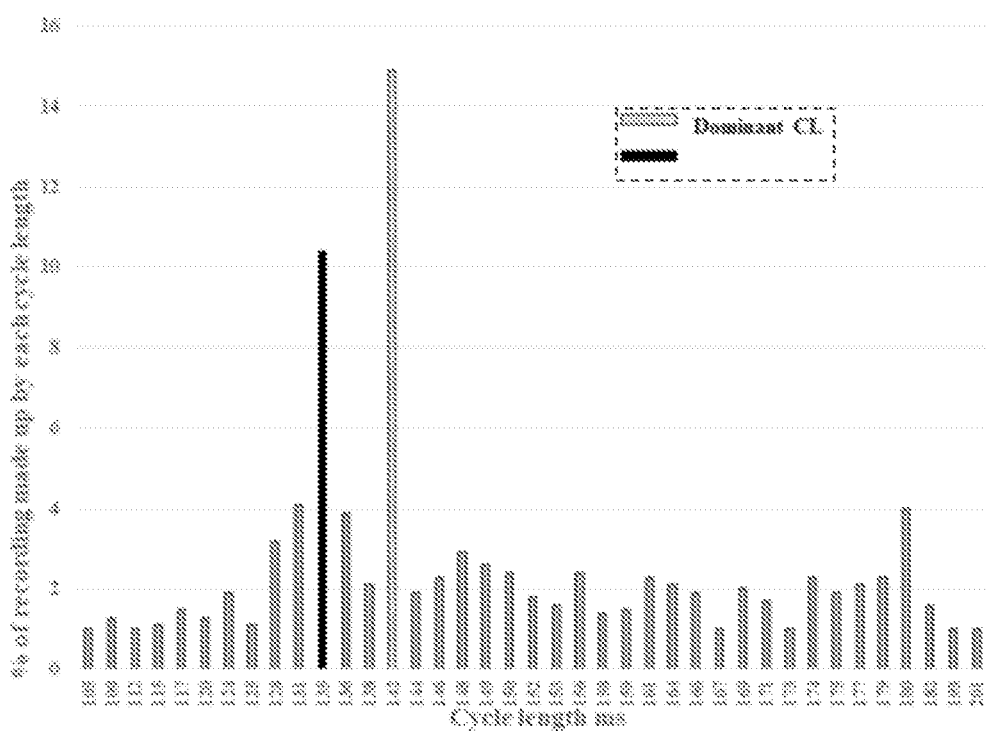
FIGS. 5A and 5B are cycle length (CL) histograms obtained at a basket catheter electrode.
Figure 5B:
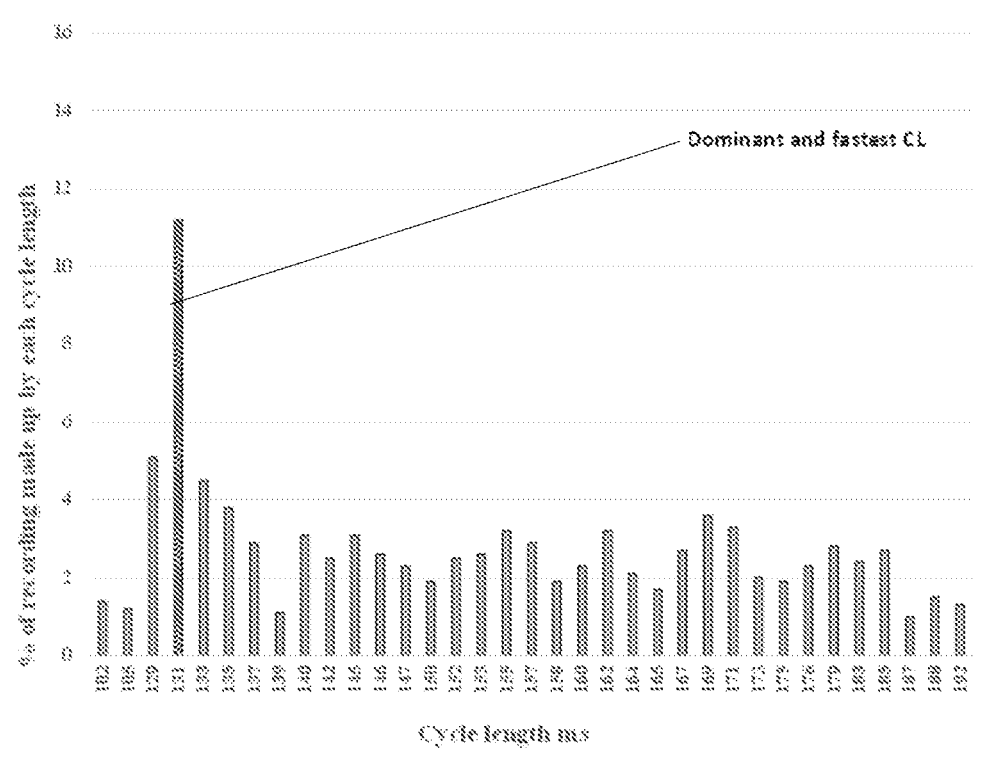

FIGS. 5A and 5B show cycle length (CL) histograms obtained at one of the basket catheter electrodes, with percentage of recording made up by each CL on the y-axis and CL on the x-axis. Each bar represents a defined a CL. For illustrative purposes less frequent CLs along the mean were excluded. Ai—Shows the Min-CL at 131 ms which also represents the dominant CL. CL at 102 ms and 105 ms are excluded as part of the methodology as they represents CLs that are >30% of the mean CL recorded at that electrode and only represents <10% of the total recording CLs. Aii—Shows the Min-CL at 135 ms whilst the dominant CL is 142 ms. Again, the CLs at 105 ms and 109 ms are excluded as part of the methodology as per above.

Figure 6:
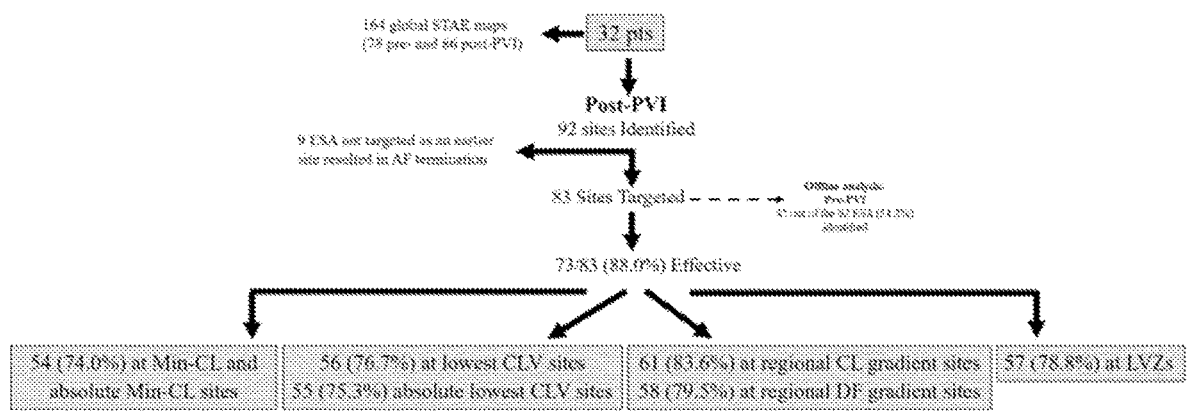
FIG. 6 is a flow diagram a study that shows the potential AFDs identified.

FIG. 6 is a flow chart of a study that shows the potential AFDs identified and those associated with an ablation response and how many of these co-located to sites of Min-CL, lowest CLV, regional DF gradients and LVZs.

Figure 7A:
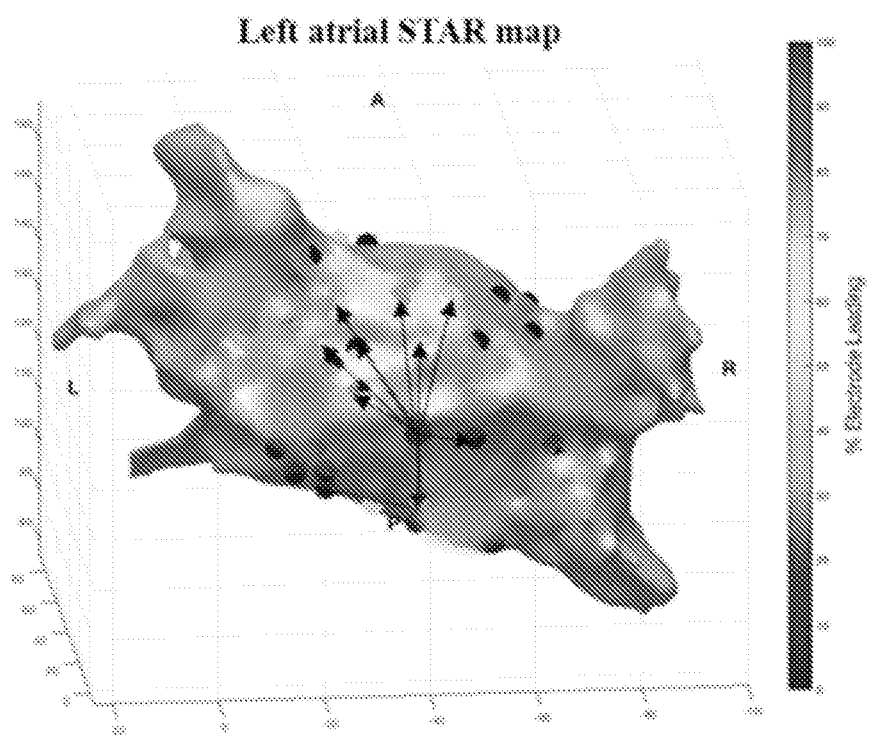
FIGS. 7A-7F are images and electrograms obtained from a subject.
Figure 7B:
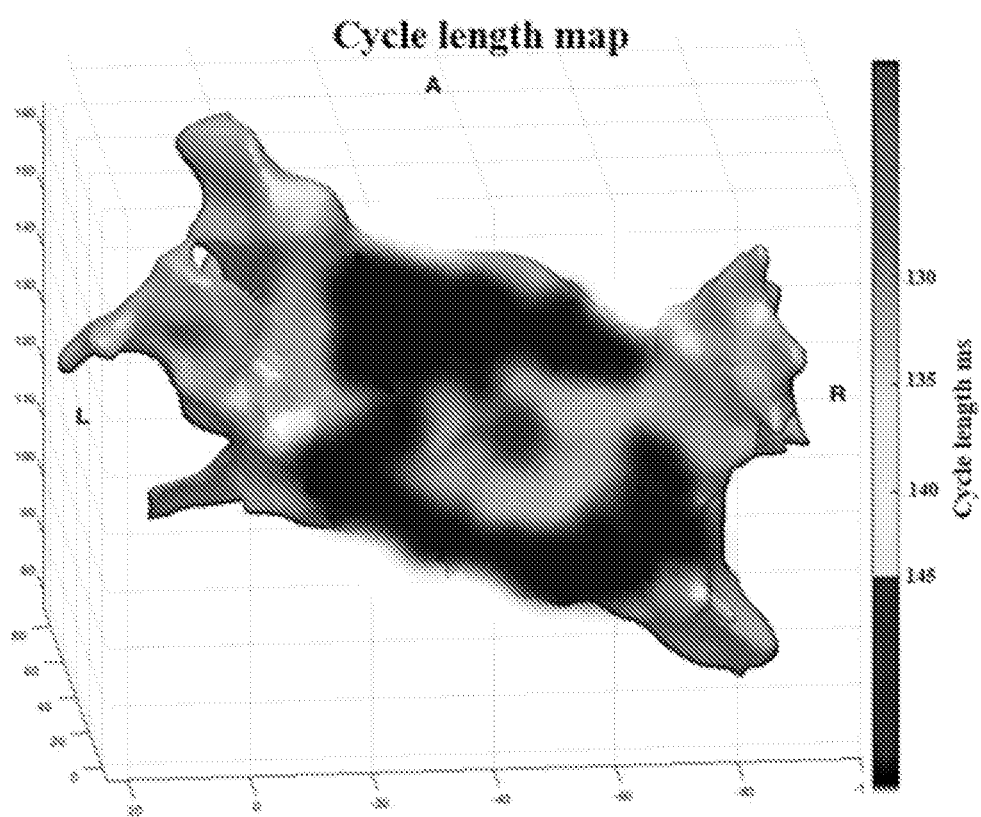
Figure 7C:
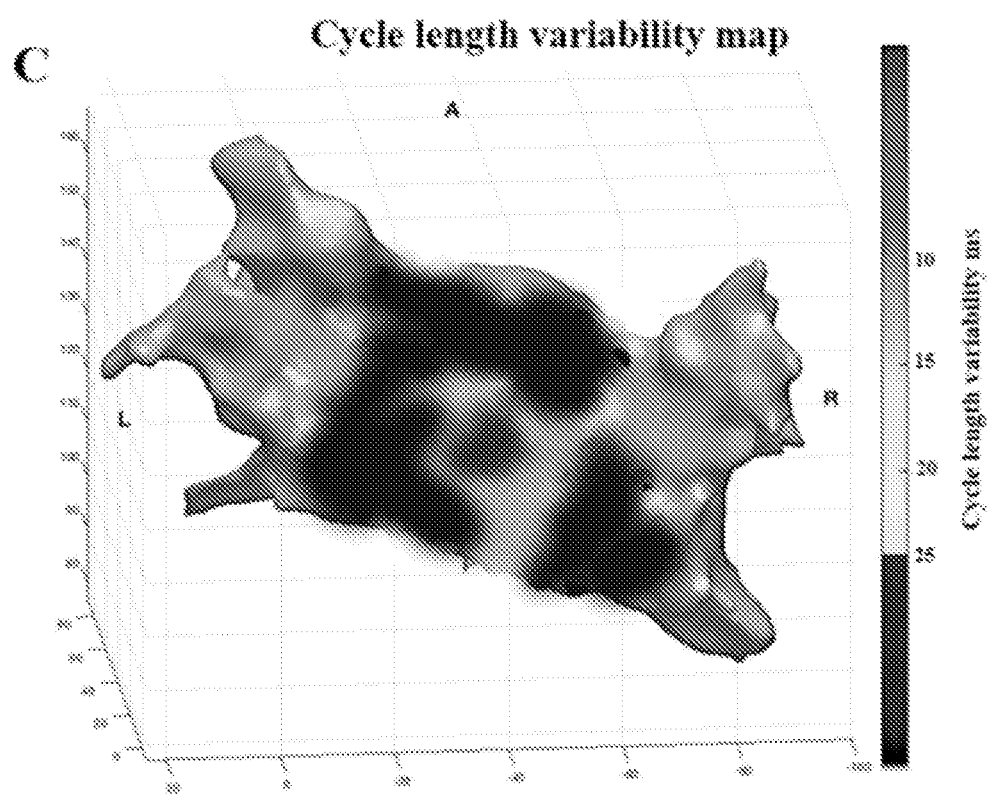
Figure 7D:
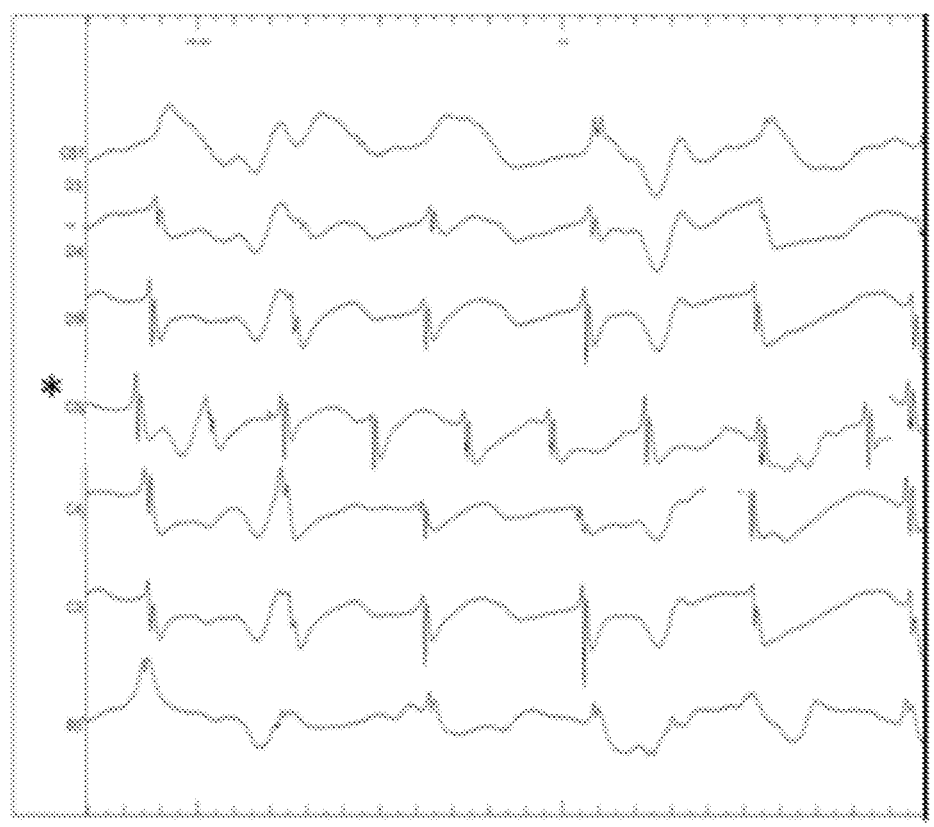
Figure 7E:
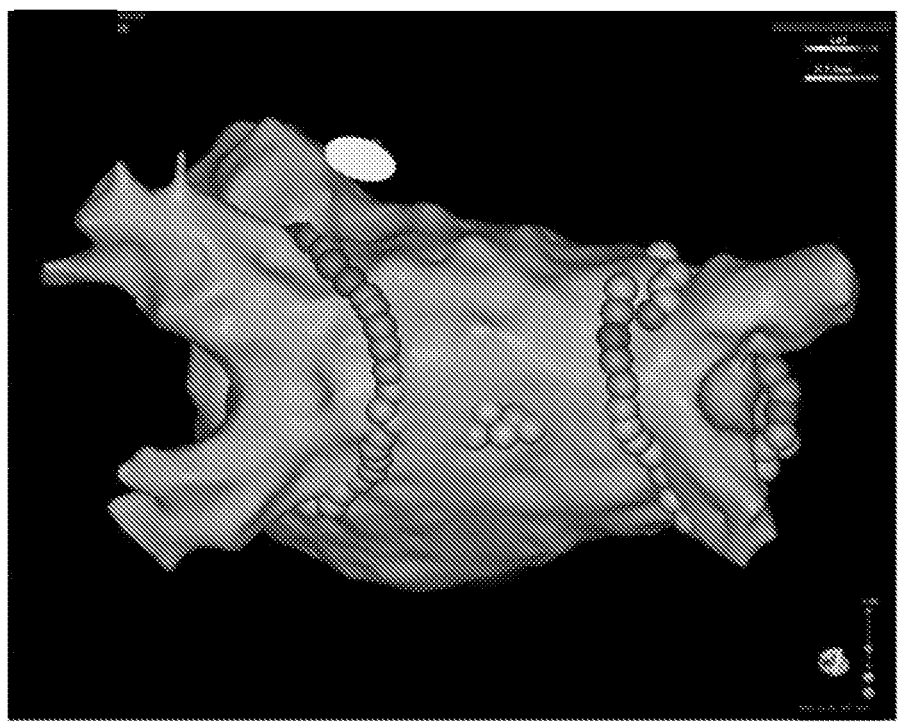
Figure 7F:

FIGS. 7A-7F are images and electrograms obtained from a subject (Patient ID 6). In FIG. 7A) STAR map of the LA in a titled roof view that shows an potential AFDs mapped to mid roof FIG. 7B) A CL map in a titled roof view demonstrates the overall fastest Min-CL at the mapped potential AFDs. FIG. 7C) A CLV map in a titled roof view demonstrates the lowest CLV at the mapped potential AFDs. FIG. 7D) Electrograms obtained at the potential AFDs (highlighted by the star) and neighboring electrodes as assigned by the STAR mapping method. The electrograms obtained at the potential AFDs demonstrates that this site is leading in comparison to its neighboring pairs and also has a faster CL. FIG. 7E) CARTO map of the LA in a roof view that demonstrates ablation at the potential AFDs as guided by the STAR map. FIG. 7F) Electrograms shows termination of AF to sinus rhythm on ablation at the potential AFDs.

Figure 8A:
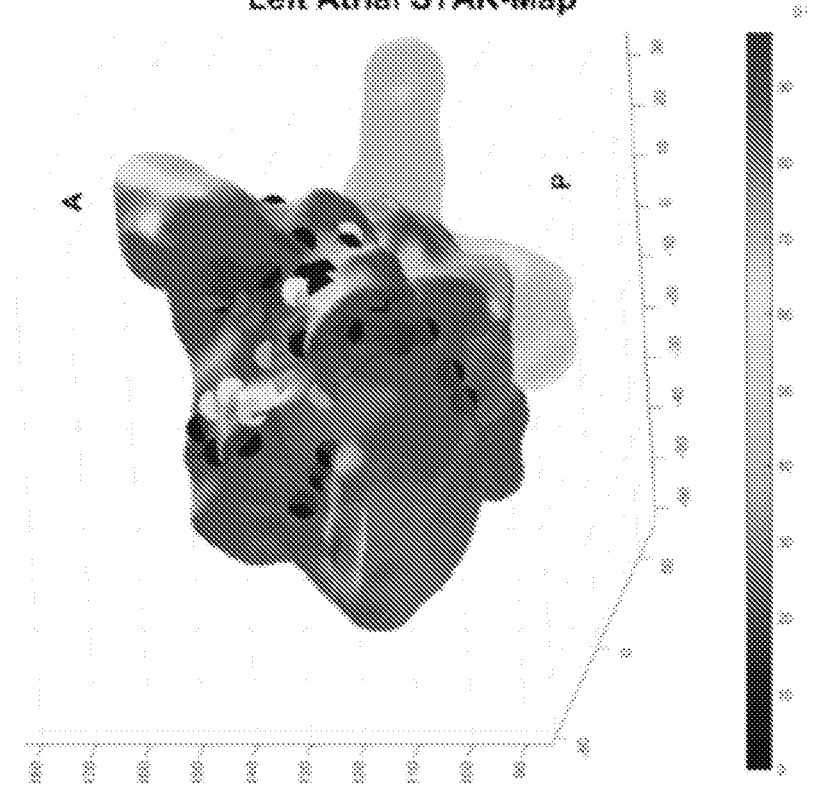
FIGS. 8A-8C are images and electrograms obtained from a subject.
Figure 8B:
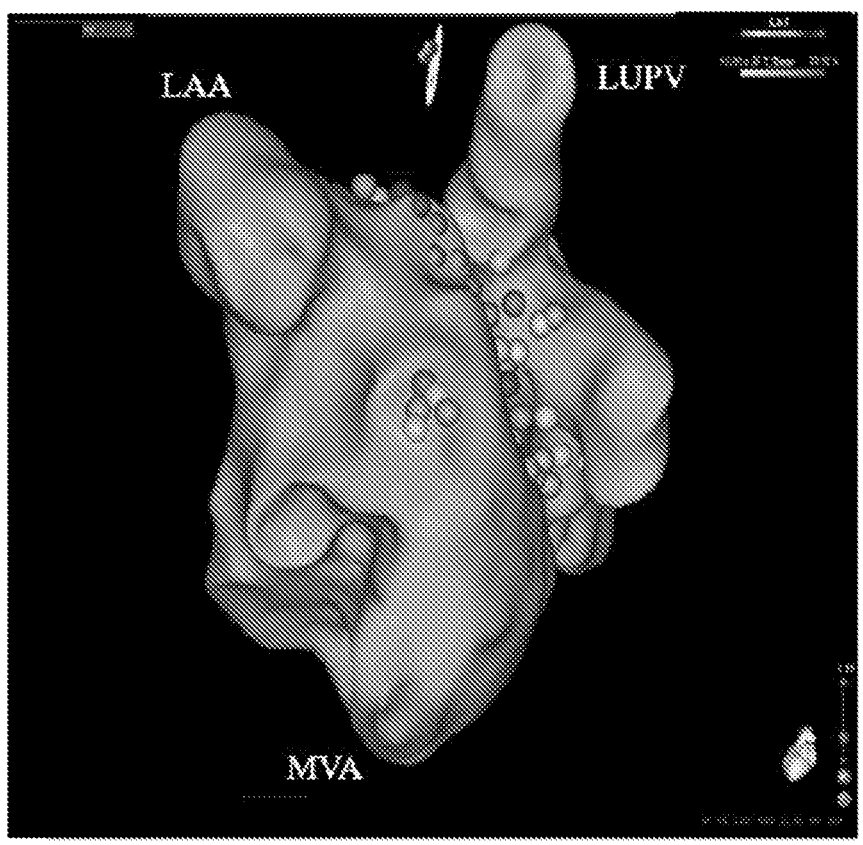
Figure 8C:
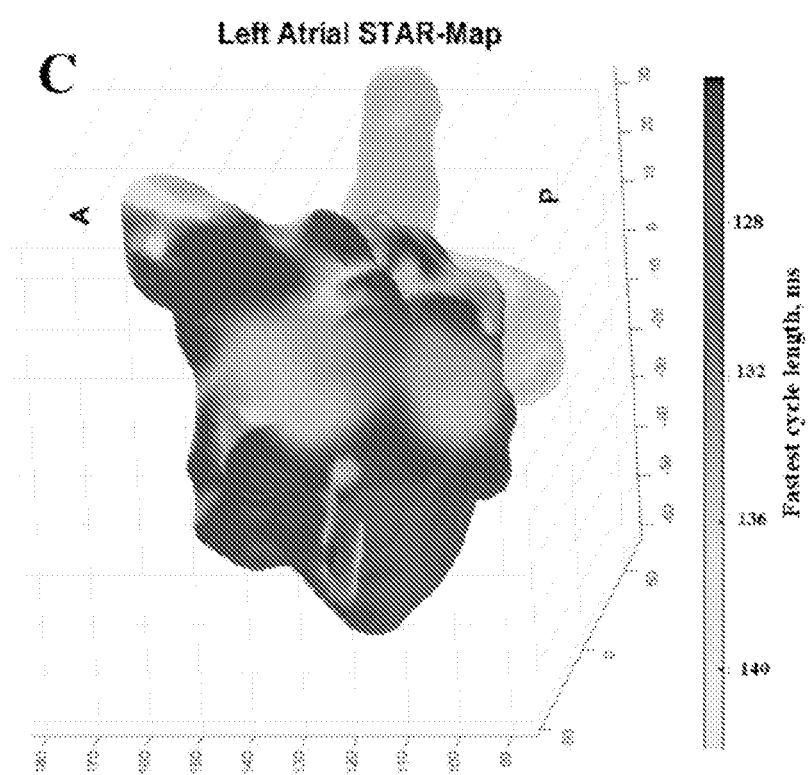

LUPV—Left upper pulmonary vein
RUPV—Right upper pulmonary vein
LAA—Left atrial appendage
MVA—Mitral valve annulus FIGS. 8A-8C are images from a different subject (Patient 16). In FIG. 8A) STAR map of the LA in a titled lateral view that shows an potential AFDs. 8B) Ablation was performed at this site as demonstrated on the CARTO LA map in a titled lateral view which resulted in termination of AF into AT. 8C) The potential AFDs co-located to the site of regional fastest CL with a reduction in CL as obtained from neighboring electrodes.

Figure 9A:
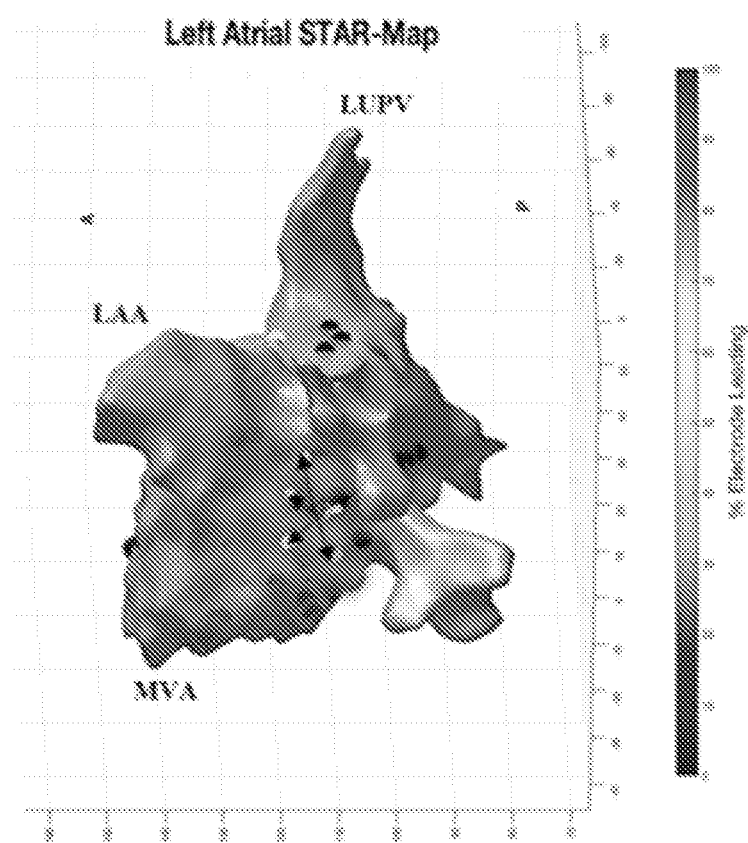
FIGS. 9A, 9B, 9C-1 and 9C-2 are images and electrograms obtained from a subject.
Figure 9B:
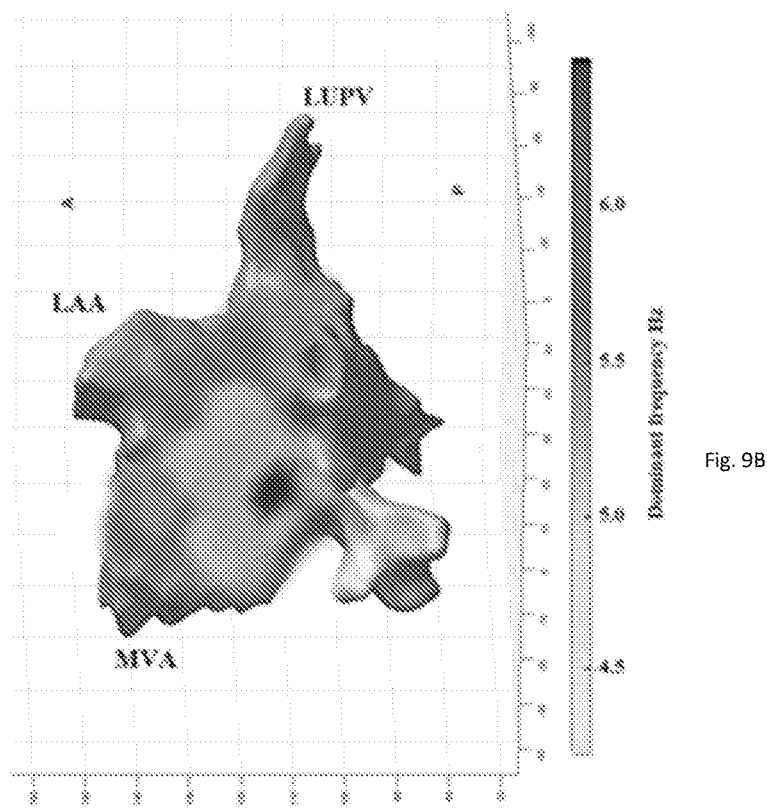
Figures 1, 9C:
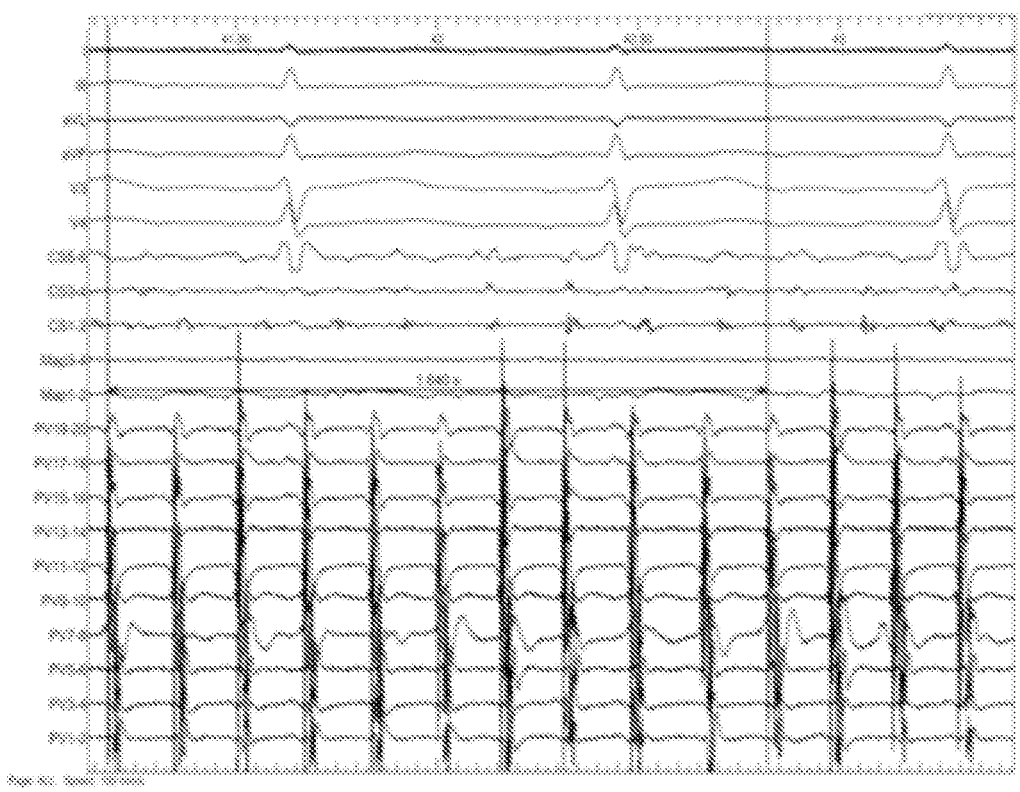
Figures 2, 9C:

LUPV—Left upper pulmonary vein
LAA—Left atrial appendage
MVA—Mitral valve annulus FIG. 9A-9C are images from yet another subject (Patient ID 18). In FIG. 9A) STAR map of the LA in a lateral view that shows an potential AFDs. 9B) The potential AFDs co-located to the site of regional highest DF with a reduction in DF as obtained from neighboring electrodes 9C-1 and 9C-2) Ablation at the potential AFDs resulted in CL slowing from 164 ms to 229 ms as shown on the electrograms obtained from BARD.

LUPV—Left upper pulmonary vein
LAA—Left atrial appendage
MVA—Mitral valve annulus Experimental Results The inventors have conducted experiments as explained below to further refine and develop STAR mapping and have established a series of parameters that may be used as modifying factors to determine further factors by which potential driver sites may be classified in terms of their importance or likelihood as being a true driver site.

Methodologies of Parameter Development

All patients had a high-density bipolar voltage map created using a PentaRay Nav catheter with 2-6-2 mm electrode spacing. Points that were >3 mm from the geometry surface were filtered as not being in contact with the myocardium, and points acquired were respiratory gated to optimize the accuracy of anatomical localization.

Parameters Examined

Bipolar Voltage and AFDs

A minimum of 800 bipolar voltage points were taken per patient with the aim to ensure adequate atrial coverage. The interpolation threshold was set to 5 mm for surface color projection and points were collected aiming for complete LA coverage (i.e. with no area >5 mm from a data point).

Areas with a bipolar voltage of <0.5 mV were defined as low voltage zones (LVZs). Voltage maps were divided into non-LVZs and LVZs. Potential AF drivers identified were then categorized as existing in either non-LVZ or LVZ. The relationship of potential AFDs mapped to LVZs and achieving AF termination on ablation was assessed. The relationship between the proportion of LVZs and number of AFDs identified was also evaluated.

Spectral Analysis and AFDs Utilizing the unipolar signals recorded from the basket catheter, the CL was determined at each electrode pole in contact over each of the 5 minutes recordings in each patient. The CL was measured as the time difference between two consecutive atrial signals using an automated custom written Matlab script. A custom algorithm was used to model plausible biological behaviour based on well described refractory periods. This algorithm was used to avoid double-counting of fractionated electrograms. Unipolar activation timing was taken as the maximum negative deflection (peak negative dv/dt).

A histogram of the CLs with all CLs identified on the x-axis (rounded to the nearest whole millisecond) and the percentage of recording made up by each CL on the y-axis were plotted for each individual electrode for each 5-minute recording for each patient. Different methods have been used previously to identify sites of rapid activity from atrial CL measurements. One approach uses a histogram of CLs and takes the center of the narrowest range of CLs in the histogram containing 50% of the cycles and defines this as the 'dominant CL'. The dominant CL for each electrode was then projected on to a replica of the anatomical geometry to identify the sites of the fastest dominant CL, as defined as the values in the top decile, and evaluate their spatial relationship to AFDs.

For the novel methodology to determine site(s) of fastest CL defined as minimum CL (Min-CL), initially extreme CL outliers were disregarded which were defined as CLs 30% slower or faster than the mean CL at the electrode and those CLs containing <10% of the cycles. From the remaining CLs, the Min-CL was identified for each electrode (FIG. 1). The Min-CL was therefore the shortest CL constituting >10% of cycles after removal of outliers. The Min-CL were compared amongst all electrodes to identify the site(s) of the overall fastest Min-CL in the LA. Two definitions of the overall fastest Min-CL were tested: i) the Min-CLs within the top decile of all electrodes and/or ii) the single shortest overall Min-CL or 'Absolute Min-CL' and any other point with a Min-CL within 5% of the overall fastest Min-CL. The position of the electrode(s) with the fastest overall Min-CL was then identified on the same STAR map that demonstrated the ESA to ensure accurate anatomical correlation.

CL variability (CLV) was used as the marker of organization. The CLV was determined for each electrode by taking the standard deviation (SD) of CLs. A smaller CLV therefore denotes less CL variation. CLV was compared amongst all electrodes to identify the site of overall lowest CLV in the LA. The sites of lowest CLV was defined as i) CLVs in the lowest decile and/or ii) CLVs within 5% of the overall lowest CLV, termed the absolute lowest CLV. The position of the electrode(s) with the lowest CLV was then identified on the STAR map and again correlated to the AFDs.

Regional CL and Frequency Gradients at Potential AFDs

The Min-CL at potential AFDs determined using the STAR mapping method were compared to the Min-CL obtained at adjacent electrodes to elicit whether there was a CL gradient from potential AFDs to surrounding areas. This was repeated for all potential AFDs identified on each STAR map in each patient. Neighboring electrodes were defined as electrodes that were within 3 cm of the potential AFDs.

To determine DF, following filtering of far-field ventricular signals, a Butterworth $2^{nd}$ order filter was applied to the unipolar signals. Rectification was then performed to take the absolute value of the signal followed by application of a low pass filter to the signal. Fourier transform was then performed with the application of a Hamming window. The DF was then determined for each four-second window. Taking the median of all these values over the 5 minutes recording the DF of the electrode poles was determined. The DFs at electrodes identified as potential AFDs were compared to the DFs obtained at adjacent electrodes to determine whether there were high-low frequency gradients from potential AFDs to surrounding areas. This was repeated for all potential AFDs identified on each STAR map in each patient. The relationship between LA site(s) with the overall highest DF, as per those values in the top decile, and potential AFDs was also assessed.

Summary Results

Thirty-two patients were included in whom 83 potential AFDs identified with STAR mapping were targeted with ablation. An ablation response was seen with 73 sites (24 AF termination and 49 CL slowing ≥30 ms). Out of the 73 sites, 54 (74.0%) and 55 (75.3%) co-located to sites of overall fastest CL and lowest CLV respectively. However, when utilizing conventional markers, the sites with the fastest dominant CL and highest DF infrequently co-located to potential AFDs with an ablation response (39, 53.4% CL and 41, 56.2% DF). PVI did not affect the CL (131.0±12.1 ms pre-PVI vs. 131.2±15.5 ms; p=0.96 post-PVI) or CLV (10.3±3.9 ms pre-PVI vs. 11.0±5.4 ms post-PVI; p=0.80) at the potential AFDs. These potential AFDs also frequently demonstrated regional CL (61/73, 83.6%) and frequency gradients (58/73, 80.8%). potential AFDs were more commonly mapped to LVZs and the proportion of LVZs correlated with the number of potential AFDs identified ($r_s$=0.91; p<0.001). Utilizing these novel markers of rapidity and organization in conjunction with STAR mapping allowed a high sensitivity and specificity in predicting which potential AFDs would produce an ablation response. Potential AFDs that co-located with sites of lowest CLV (24/24 (100%) vs. 31/49 (63.2%); p<0.001) and fastest CL (24/24 (100%) vs. 30/49 (61.2%); p<0.001) were consistently associated with AF termination on ablation rather than CL slowing.

Detailed Results

Thirty-two patients underwent STAR mapping guided ablation. The mean AF duration was 15.4±4.3 months and 21 of the 32 (65.6%) patients were on an anti-arrhythmic drug pre-ablation.

Ablation Response at Potential AFDs

In brief, 92 potential AFDs were identified in the 32 patients (2.8±0.8 per patient) on the post-PVI STAR maps of which 83 (90.2%, 2.6±0.7 per patient) were targeted with ablation (FIG. 3). The 9 potential AFDs that were not ablated were in patients in whom ablation at a previous site had resulted in AF termination.

An ablation response was achieved with 73 potential AFDs (2.3±0.6 per patient) which included at least one response in all 32 patients. On a per potential AFDs basis AF termination was achieved with ablation at 24 sites (18 organization to AT and 6 termination to sinus rhythm) and CL slowing of ≥30 ms was achieved with 49 sites. On a per patient basis, AF termination was achieved in 24 patients and CL slowing of ≥30 ms in the remaining 8 patients.

Bipolar Voltage and Potential AFDs

On a per patient basis, an average of 3.4±0.7 well defined LVZs were identified. A majority of the potential AFDs identified were mapped to LVZs (62/92, 67.4%). Out of the 83 potential AFDs that were ablated 60 were mapped to LVZs (72.3%) of which 59 (98.3%) were associated with an ablation response.

Patients with more than 50% of the LA comprised by LVZs (59.2±6.5 mV) were more likely to have more than 2 potential AFDs identified. There was a strong positive correlation between the proportion of LVZs present and the number of potential AFDs identified ($r_s$=0.91; p<0.001). However, LVZ alone was of little predictive value in predicting AFD sites.

The association of potential AFDs with a LVZ was highly predictive of a response to ablation. potential AFDs mapped to LVZs were also more frequently associated with AF termination on ablation versus potential AFDs mapped to non-LVZs (odds ratio=20.0, 95% CI 1.1-351.5; p=0.04).

Spectral Analysis and Potential AFDs

For the spectral analysis a total of 170 5-minute unipolar recordings were used. Out of these 170 recordings, 84 were created pre- and 86 post-PVI. The mean dominant CL and the mean Min-CL obtained at potential AFDs post-PVI, was 137.9±64.2 ms and 131.2±15.5 ms respectively.

Co-Location of Sites Identified on Spectral Analysis and Potential AFDs i) Fastest Dominant CL Of the 92 potential AFDs identified post-PVI, 47 (51.1%) co-located to sites of fastest dominant CL(s). Dominant CL showed a sensitivity of 51.1% (95% CI 40.4-61.7%) and specificity of 18.6% (95% CI 8.4-33.4%) in predicting an AFD. The positive and negative predictive values were 57.3% (95% CI 51.2-63.2%) and 15.1% (95% CI 8.4-25.6%) respectively.

ii) Min-CL Sites within the Top Decile and the Absolute Min-CL

On a per patient basis, an average of 4.1±1.1 Min-CL sites were identified in the top decile. Out of the 92 potential AFDs identified post-PVI, 58 (63.0%) co-located to one of these sites. Min-CL sites, as per those in the top decile showed a sensitivity of 63.0% (95% CI 52.3-72.9) and specificity of 20.4% (95% CI 10.2-34.3) in identifying potential AFDs.

On a per patient basis, an average of 2.5±0.9 absolute Min-CL sites were identified that were within 5% of the fastest Min-CL site. Out of the 92 potential AFDs identified post-PVI, 56 (60.9%) co-located to one of these sites.

iii) Lowest CLV Sites within the Lowest Decile and Absolute Lowest CLV

On a per patient basis, an average of 3.8±1.0 lowest CLV sites were identified in the lowest decile. Out of the 92 potential AFDs identified post-PVI, 61 (66.3%) co-located to one of these sites. Lowest CLV, as per those in the lowest decile showed a sensitivity of 66.3% (95% CI 55.7-75.8) and specificity of 24.4% (95% CI 12.4-40.3) in identifying potential AFDs.

On a per patient basis, an average of 2.3±0.8 lowest CLV sites were identified that were within 5% of the overall lowest CLV site. Out of the 92 potential AFDs identified post-PVI, 60 (65.2%) co-located to one of these sites.

Use of Spectral Analysis to Predict Response to Ablation at Potential AFDs i) Fastest Dominant CL Out of the 73 potential AFDs that were associated with an ablation response only 39 (53.4%) co-located to a site of fastest dominant CL. Fastest dominant CL showed a sensitivity of 53.4% (95% CI 41.4-65.2%) and specificity of 26.3% (95% CI 13.4-43.1%) in predicting a potential AFD. The positive and negative predictive values were 58.2% (95% CI 51.1-65.0%) and 22.7% (95% CI 14.1-34.6%) respectively.

ii) Min-CL Sites within the Top Decile and the Absolute Min-CL

Out of the 73 potential AFDs with a study-defined ablation response 54 (74.0%) co-located to one of the Min-CL sites (FIG. 3 and FIG. 4A-F).

Co-locating to these sites was again shown to demonstrate a high diagnostic accuracy in predicting potential AFDs with an ablation response.

iii) Lowest CLV Sites within the Lowest Decile and Absolute Lowest CLV

Out of the 73 potential AFDs with a study-defined ablation response 56 (76.7%) co-located to one of the lowest CLV sites as defined within the lowest decile (FIG. 5 and FIG. 6A-F).

Out of the 73 potential AFDs that was associated with an ablation response 55 (75.3%) co-located to one of the absolute lowest CLV sites (FIG. 4 and FIG. 6A-F). Co-locating to these sites was again shown to demonstrate a high diagnostic accuracy in predicting potential AFDs with an ablation response.

iv) Predicting AF Termination potential AFDs that co-located with sites of Min-CL as per either definition were more frequently associated with AF termination on ablation in contrast to CL slowing (24/24 (100%) vs. 29/49 (59.2%); p<0.001). This marker showed an odds ratio of 34.1 (95% CI 2.0-592.3; p=0.02) for predicting AF termination on ablation at an AFD.

potential AFDs that co-located with sites of lowest CLV as per either definition were more frequently associated with AF termination on ablation in contrast to CL slowing (24/24 (100%) vs. 31/49 (63.2%); p<0.001). This marker showed an odds ratio of 28.8 (95% CI 1.7-501.6; p=0.02) for predicting AF termination on ablation at an potential AFDs.

Regional CL and Frequency Gradients and Potential AFDs

Out of the 92 potential AFDs identified there was a clear gradient in min-CL from the potential AFDs to the surrounding poles with 56 potential AFDs (60.9%) (FIG. 5 and FIG. 8A-D). Out of the 73 potential AFDs with an ablation response 61 (83.6%) demonstrated a fastest-slowest Min-CL gradient from the potential AFDs to neighboring poles. The mean reduction in Min-CL from the potential AFDs to the neighboring poles within 3 cm was 10.5±4.2 ms (p=0.01). The presence of a regional CL gradient at potential AFDs showed an odd ratio of 5.1 (95% CI 1.3-20.3, p=0.02) in predicting potential AFDs with an ablation response.

The mean DF at the potential AFDs was 6.2±0.7 Hz. potential AFDs only co-located to sites of highest DF in the LA in 56.5% of cases (52/92) of which 41 out the 73 (56.2%) with an ablation response co-located to sites of highest DF. Out of the 92 potential AFDs identified there was a clear frequency gradient from the potential AFDs to the neighboring poles with 59 potential AFDs (64.1%) (FIG. 5 and FIG. 7A-D). The mean reduction in DF from the potential AFDs to the neighboring poles was 1.8±0.7 Hz (p=0.01). When only reviewing the 73 potential AFDs with an ablation response, 58 (80.8%) demonstrated a frequency gradient. The presence of a regional frequency gradient at potential AFDs showed an odd ratio of 5.8 (95% CI 1.4-23.2, p=0.01) in predicting potential AFDs with an ablation response. The presence of a frequency gradient was not significantly different in those with AF termination vs. those with CL slowing on ablation (18/24, 75.0% vs. 39/49, 79.6%; p=0.78).

Impact of PVI on Spectral Analysis Data

Of the 92 potential AFDs that were identified post-PVI, 42 were also detected on the pre-PVI maps of which 39 (92.9%) were associated with a study-defined ablation response. The mean CLV pre-PVI (obtained through taking the average CLV of all electrodes) was lower in those patients that had potential AFDs identified both pre-PVI compared to those that only had potential AFDs identified post-PVI (31.4±4.8 ms vs. 49.5±7.3 ms; p=0.01).

PVI did not affect the CL (131.0±12.1 ms pre-PVI vs. 131.2±15.5 ms; p=0.96 post-PVI) and CLV (10.3±3.9 ms pre-PVI vs. 11.0±5.4 ms post-PVI; p=0.80) at the potential AFDs.

potential AFDs that were also identified pre-PVI showed a sensitivity of 53.4% (95% CI 41.4-65.2) and specificity of 90.0% (95% CI 55.5-99.8) in predicting potential AFDs with an ablation response. The positive and negative predictive value was 97.5% (95% CI 85.7-99.6) and 20.9% (95% CI 16.1-26.7) respectively.

It is to be appreciated that certain embodiments of the invention as discussed below may be incorporated as code (e.g., a software algorithm or program) residing in firmware and/or on computer useable medium having control logic for enabling execution on a computer system having a computer processor. Such a computer system typically includes memory storage configured to provide output from execution of the code which configures a processor in accordance with the execution. The code can be arranged as firmware or software, and can be organized as a set of modules such as discrete code modules, function calls, procedure calls or objects in an object-oriented programming environment. If implemented using modules, the code can comprise a single module or a plurality of modules that operate in cooperation with one another.

Optional embodiments of the invention can be understood as including the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth.

Although illustrated embodiments of the present invention have been described, it should be understood that various changes, substitutions, and alterations can be made by one of ordinary skill in the art without departing from the present invention which is defined by the recitations in the claims below and equivalents thereof.

This application claims priority from GB 1915680.1, the content of which and the content of the abstract filed herewith is hereby incorporated by reference.

The invention claimed is:

1. A computer implemented method to identify one or more regions of the heart responsible for supporting or initiating abnormal heart rhythms, the computer implemented method using electrogram data recorded from a plurality of electrodes on multipolar cardiac catheters obtained from a corresponding series of sensing locations on the heart over a recording time period, the method comprising the steps of:
   identifying, from the electrograms, regions within a chamber of the heart which have electrical activation sequences which characterize them as potential drivers of abnormal heart rhythms,
   for each sensing location at or substantially about said region, determining from predominant activations, an earliest activating electrode site;
   for each determined earliest activating electrode site:
   calculating a value for each of a plurality of modifiers associated with the electrode site, the modifiers being determined from the electrogram data for the site, tissue characteristics of the site or anatomical characteristics of the site;
   determining a ranking factor calculated from the plurality of modifiers;
   ranking the each of said earliest activating electrode sites in dependence on its ranking factor; and
   outputting data identifying said regions, the data varying prominence of each of the determined earliest activating electrode sites in dependence on said ranking, wherein the modifiers determined from electrogram data include:
   the minimum cycle length of electrograms recorded at that electrode, the gradient in activation frequency between electrograms recorded at that electrode or within that region and electrograms obtained within a pre-defined geodesic distance, and the average voltage of local electrograms recorded within that region.

2. The computer-implemented method of claim 1, wherein a modifier on tissue characteristics includes a measure of presence and density of scar tissue determined by imaging.

3. The computer implemented method of claim 1, wherein the outputting data comprises displaying the data with a visual indication that varies in prominence for each of the determined earliest activating electrode sites in dependence on said ranking.

4. The computer implemented method of claim 1, further comprising outputting data to a display or medical scanning device to cause display or navigation of chamber geometry and to guide placement of catheters or electrodes for a subsequent electrogram data acquisition.

5. The computer implemented method of claim 4, further comprising identifying a site for subsequent placement of the catheters or electrodes to eliminate or confirm a previously determined first activating electrode or to extend the electrogram data to a previously unscanned or incompletely scanned region.

6. The computer implemented method of claim 5, further comprising identifying the site from the location of first activating sites already identified or from vectors of activation and gradients in signal leading scores.

7. The computer implemented method of claim 1, further comprising receiving electrogram data in substantially real-time and providing an indication as to when sufficient timing of acquisition has been undertaken for the respective site.

8. The computer implemented method of claim 7, wherein the step of determining whether sufficient timing of acquisition has been undertaken comprises one or more of: counting down a predetermined time period, acquiring a pre-set number of activation cycles on at least a minimum of a pre-set number of electrodes on the roving multipolar mapping catheter, and acquiring a predetermined time or predetermined number of activation cycles where the pattern of activation across multiple electrodes remains within a pattern-matched sequence.

9. The computer implemented method of claim 7, wherein the step of determining whether sufficient timing of acquisition has been undertaken comprises determining that an activation pattern of the site being scanned has reached a predetermined level of statistical certainty.

10. A computer implemented method to identify one or more regions of the heart responsible for supporting or initiating abnormal heart rhythms, the computer implemented method using electrogram data recorded from a plurality of electrodes on multipolar cardiac catheters obtained from a corresponding series of sensing locations on the heart over a recording time period, the method including the steps of:
   identifying, from the electrograms, regions within a chamber of the heart which have electrical activation sequences which characterize them as potential drivers of abnormal heart rhythms,
   for each sensing location at or substantially about said region, determining from predominant activations, an earliest activating electrode site;
   for each determined earliest activating electrode site:
   calculating a value for each of a plurality of modifiers associated with the electrode site, the modifiers being determined from the electrogram data for the site, tissue characteristics of the site or anatomical characteristics of the site;
   determining a ranking factor calculated from the plurality of modifiers;
   ranking the each of said earliest activating electrode sites in dependence on its ranking factor; and,
   outputting data identifying said regions, the data varying prominence of each of the determined earliest activating electrode sites in dependence on said ranking wherein a modifier on tissue characteristics includes a measure of tissue impedance at that site.

11. A computer implemented method to identify one or more regions of the heart responsible for supporting or initiating abnormal heart rhythms, the computer implemented method using electrogram data recorded from a plurality of electrodes on multipolar cardiac catheters obtained from a corresponding series of sensing locations on the heart over a recording time period, the method including the steps of:
   identifying, from the electrograms, regions within a chamber of the heart which have electrical activation sequences which characterize them as potential drivers of abnormal heart rhythms,
   for each sensing location at or substantially about said region, determining from predominant activations, an earliest activating electrode site;
   for each determined earliest activating electrode site:
   calculating a value for each of a plurality of modifiers associated with the electrode site, the modifiers being determined from the electrogram data for the site, tissue characteristics of the site or anatomical characteristics of the site;

determining a ranking factor calculated from the plurality of modifiers;

ranking the each of said earliest activating electrode sites in dependence on its ranking factor; and, outputting data identifying said regions, the data varying prominence of each of the determined earliest activating electrode sites in dependence on said ranking wherein a modifier is determined from results of treatment at another earliest activating electrode site.

12. A computer implemented method to identify one or more regions of the heart responsible for supporting or initiating abnormal heart rhythms, the computer implemented method using electrogram data recorded from a plurality of electrodes on multipolar cardiac catheters obtained from a corresponding series of sensing locations on the heart over a recording time period, the method including the steps of:

identifying, from the electrograms, regions within a chamber of the heart which have electrical activation sequences which characterize them as potential drivers of abnormal heart rhythms, for each sensing location at or substantially about said region, determining from predominant activations, an earliest activating electrode site;

for each determined earliest activating electrode site:

calculating a value for each of a plurality of modifiers associated with the electrode site, the modifiers being determined from the electrogram data for the site, tissue characteristics of the site or anatomical characteristics of the site;

determining a ranking factor calculated from the plurality of modifiers;

ranking the each of said earliest activating electrode sites in dependence on its ranking factor; and, outputting data identifying said regions, the data varying prominence of each of the determined earliest activating electrode sites in dependence on said ranking wherein a modifier on tissue characteristics is calculated by reference to the results of ablation at similar sites in previous cases.

13. A computer implemented method to identify one or more regions of the heart responsible for supporting or initiating abnormal heart rhythms, the computer implemented method using electrogram data recorded from a plurality of electrodes on multipolar cardiac catheters obtained from a corresponding series of sensing locations on the heart over a recording time period, the method including the steps of:

identifying, from the electrograms, regions within a chamber of the heart which have electrical activation sequences which characterize them as potential drivers of abnormal heart rhythms, for each sensing location at or substantially about said region, determining from predominant activations, an earliest activating electrode site;

for each determined earliest activating electrode site:

calculating a value for each of a plurality of modifiers associated with the electrode site, the modifiers being determined from the electrogram data for the site, tissue characteristics or anatomical characteristics of the site;

determining a ranking factor calculated from the plurality of modifiers;

ranking the each of said earliest activating electrode sites in dependence on its ranking factor; and, outputting data identifying said regions, the data varying prominence of each of the determined earliest activating electrode sites in dependence on said ranking wherein a modifier on anatomical characteristics comprises a predetermined weighting factor that depends on the location of the electrode site.

14. A computer implemented method to identify one or more regions of the heart responsible for supporting or initiating abnormal heart rhythms, the computer implemented method using electrogram data recorded from a plurality of electrodes on multipolar cardiac catheters obtained from a corresponding series of sensing locations on the heart over a recording time period, the method including the steps of:

identifying, from the electrograms, regions within a chamber of the heart which have electrical activation sequences which characterize them as potential drivers of abnormal heart rhythms, for each sensing location at or substantially about said region, determining from predominant activations, an earliest activating electrode site;

for each determined earliest activating electrode site:

calculating a value for each of a plurality of modifiers associated with the electrode site, the modifiers being determined from the electrogram data for the site, tissue characteristics of the site or anatomical characteristics of the site;

determining a ranking factor calculated from the plurality of modifiers;

ranking the each of said earliest activating electrode sites in dependence on its ranking factor; and, outputting data identifying said regions, the data varying prominence of each of the determined earliest activating electrode sites in dependence on said ranking wherein the site is classified as an earliest activating electrode site if activation occurs across at least 2 electrodes subtending less than a predefined angle from the vertex subtended by the potential driver site, and at least one electrogram activation is determined as later than the potential driver site within a defined arc of excitable tissue.

15. The computer implemented method of claim 14, wherein the predefined angle is less than 180 degrees.

16. A computer implemented method to identify one or more regions of the heart responsible for supporting or initiating abnormal heart rhythms, the computer implemented method using electrogram data recorded from a plurality of electrodes on multipolar cardiac catheters obtained from a corresponding series of sensing locations on the heart over a recording time period, the method including the steps of:

identifying, from the electrograms, regions within a chamber of the heart which have electrical activation sequences which characterize them as potential drivers of abnormal heart rhythms, for each sensing location at or substantially about said region, determining from predominant activations, an earliest activating electrode site;

for each determined earliest activating electrode site:

calculating a value for each of a plurality of modifiers associated with the electrode site, the modifiers being determined from the electrogram data for the site, tissue characteristics of the site or anatomical characteristics of the site;

determining a ranking factor calculated from the plurality of modifiers;

ranking the each of said earliest activating electrode sites in dependence on its ranking factor; and, outputting data identifying said regions, the data varying prominence of each of the determined earliest activating electrode sites in dependence on said ranking further comprising deriving wavefront directions by determining which electrode in every electrode pair is leading, and processing the wavefront direction to determine if the earliest activating electrode is a true AFD or represents a passively activating site activated from beyond the boundary of measurement.

17. A computer implemented method for analyzing electrograms acquired from the heart to identify one or more regions of the heart responsible for supporting or initiating abnormal heart rhythms, the computer implemented method using electrogram data recorded from a plurality of electrodes on multipolar cardiac catheters obtained from a corresponding series of sensing locations on the heart over a recording time period, the method comprising the steps of:

defining specific regions within a chamber of the heart as potential drivers of abnormal heart rhythms by analysis of electrical activation sequences, weighting classification of a region as a potential driver according to factors including if:

the direction of the activation generated wavefront is progressing from the potential driver site to one or more nearby electrodes compared to that driver site during the same acquisition;

the sequence and timing of activation is within a biologically plausible manner, with reference to conduction velocities and paths being within plausible activation sequence;

activation occurs across at least 2 electrodes subtending less than a defined angle, from the vertex subtended by the potential driver site, and at least one electrogram activation is determined as later than the potential driver site within a defined arc of excitable tissue, and a further acquisition performed in an adjacent location subtending the missing arc of the first potential driver site does not fail to confirm a potential driver site at a similar location, and displaying refined potential drivers in a highlighted manner according to the weighting, the display being in relation to a computer representation of the heart chamber.

18. A computer system for identifying one or more areas of the heart muscle responsible for supporting or initiating abnormal heart rhythms using electrogram data recorded from a plurality of electrodes on multipolar cardiac catheters obtained from a corresponding series of sensing locations on the heart over a recording time period, the system comprising:

a processor;

a first memory for storing received electrogram data; and a second memory having program code stored therein that when executed by the processor causes the system to:

identify, from the electrograms, regions within a chamber of the heart which have electrical activation sequences which characterize them as potential drivers of abnormal heart rhythms, for each sensing location at or substantially about said region, determining from predominant activations, an earliest activating electrode site;

for each determined earliest activating electrode site:

calculating a value for each of a plurality of modifiers associated with the electrode site, the modifiers being determined from the electrogram data for the site, tissue characteristics of the site or anatomical characteristics of the site;

determine a ranking factor calculated from the plurality of modifiers;

rank the each of said earliest activating electrode sites in dependence on its ranking factor; and output data identifying said regions, the data varying prominence of each of the determined earliest activating electrode sites in dependence on said ranking wherein the program code when executed by the processor causes the system to determine the modifiers determined from electrogram data including one or more of: the minimum cycle length of electrograms recorded at that electrode, the gradient in activation frequency between electrograms recorded at that electrode or within that region and electrograms obtained within a pre-defined geodesic distance, and the average voltage of local electrograms recorded within that region.

19. The computer system of claim 18, wherein the program code when executed by the processor causes the system to determine the modifiers on tissue characteristics by obtaining a measure of presence and density of scar tissue determined by imaging.

20. The computer system of claim 18, wherein the program code when executed by the processor causes the system to determine the modifiers on tissue characteristics by obtaining a measure of tissue impedance at that site.

21. The computer system of claim 18, wherein the program code when executed by the processor causes the system to determine the modifiers on tissue characteristics by obtaining from results of treatment at another earliest activating electrode site.

22. The computer system of claim 18, wherein the program code when executed by the processor causes the system to determine a modifier on tissue characteristics by accessing data on the results of ablation at similar sites in previous cases.

23. The computer system of claim 18, wherein the program code when executed by the processor causes the system to determine a modifier by accessing data to obtain a predetermined weighting factor that depends on the location of the electrode site.

24. The computer system of claim 18, wherein the program code when executed by the processor causes the system to cause output of a visual indication that varies in prominence for each of the determined earliest activating electrode sites in dependence on said ranking.

25. The computer system of claim 18, wherein the program code when executed by the processor causes the system to cause output of data to a display or medical scanning device to cause display or navigation of chamber geometry and to guide placement of catheters or electrodes for a subsequent electrogram data acquisition.

* * * * *